US010946050B2

(12) United States Patent
Lin et al.

(10) Patent No.: US 10,946,050 B2
(45) Date of Patent: Mar. 16, 2021

(54) COMPOSITIONS COMPRISING PROBIOTICS AND METHODS OF USE THEREOF

(71) Applicant: Imagilin Technology LLC, Frederick, MD (US)

(72) Inventors: Jhy-Jhu Lin, Potomac, MD (US); Jolinta Lin, Baltimore, MD (US)

(73) Assignee: IMAGILIN TECHNOLOGY LLC, Frederick, MD (US)

( * ) Notice: Subject to any disclaimer, the term of this patent is extended or adjusted under 35 U.S.C. 154(b) by 0 days.

(21) Appl. No.: 15/365,916

(22) Filed: Nov. 30, 2016

(65) Prior Publication Data

US 2017/0143777 A1 May 25, 2017

Related U.S. Application Data

(63) Continuation-in-part of application No. 15/072,308, filed on Mar. 16, 2016, now Pat. No. 10,195,237.

(60) Provisional application No. 62/386,347, filed on Nov. 30, 2015, provisional application No. 62/177,468, filed on Mar. 16, 2015.

(51) Int. Cl.
| | | |
|---|---|---|
| *A61K 35/744* | (2015.01) | |
| *A61K 35/00* | (2006.01) | |
| *A23L 25/00* | (2016.01) | |
| *A23L 3/00* | (2006.01) | |

(52) U.S. Cl.
CPC .............. *A61K 35/744* (2013.01); *A23L 3/00* (2013.01); *A23L 25/00* (2016.08); *A23V 2002/00* (2013.01); *A23Y 2280/15* (2013.01); *A61K 2035/115* (2013.01)

(58) Field of Classification Search
CPC ... A61K 35/744; A61K 2035/115; A23L 3/00; A23Y 2280/15
See application file for complete search history.

(56) References Cited

U.S. PATENT DOCUMENTS

| | | | |
|---|---|---|---|
| 6,692,779 | B2 | 2/2004 | Dominques |
| 7,579,030 | B2 | 8/2009 | Domingues |
| 7,935,334 | B2 | 5/2011 | Lin |
| 8,318,152 | B2 | 11/2012 | Lin |
| 8,496,923 | B2 | 7/2013 | Lin |
| 9,289,008 | B1 | 3/2016 | Lin |
| 9,364,507 | B2 | 6/2016 | Lin |
| 9,789,141 | B2 | 10/2017 | Lin |
| 2006/0008511 | A1 | 1/2006 | Lin |
| 2007/0207133 | A1* | 9/2007 | Wassell ................ A23D 7/0053 424/93.45 |
| 2009/0263366 | A1* | 10/2009 | Lin ...................... A61K 35/744 424/93.44 |
| 2010/0094243 | A1 | 4/2010 | Wiggins |
| 2013/0064885 | A1 | 3/2013 | Lin |
| 2013/0101566 | A1 | 4/2013 | Mazo et al. |
| 2014/0093614 | A1* | 4/2014 | Gonzalez .............. A23L 1/3014 426/61 |
| 2014/0193464 | A1 | 7/2014 | Lin |
| 2015/0246082 | A1 | 9/2015 | Lin |
| 2016/0193259 | A1 | 7/2016 | Lin |
| 2016/0243173 | A1 | 8/2016 | Lin |
| 2017/0020929 | A1 | 1/2017 | Lin |

FOREIGN PATENT DOCUMENTS

| | | |
|---|---|---|
| CN | 104472426 A | 4/2015 |
| JP | 62232334 A | 3/1986 |
| JP | 2003334065 A | 11/2003 |
| JP | 2007529214 A | 10/2007 |
| JP | 2009514515 A | 4/2009 |
| JP | 2013505257 A | 4/2013 |
| JP | 2017012157 A | 1/2017 |
| WO | 2006053445 A1 | 5/2006 |
| WO | 2017095968 A1 | 6/2017 |

OTHER PUBLICATIONS

Product Safety Sumary Sheet. Dupont Lecithins. p. 1-3 (Year: 2012).*
International Search Report from international Appl. No. PCT/US2016/064286 dated Mar. 23, 2017.
MitoMax—premium probiotics for dogs and cats, (2017). downloaded from www.amazon.com/MitoMax-premium-probiotics-dogs-capsules-bottle/dp/B003NH02DW. p. 1 (Year: 2017).
U.S. Office Action from U.S. Appl. No. 15/072,308, dated Nov. 14, 2017.
U.S. Office Action from U.S. Appl. No. 15/072,308, dated Apr. 6, 2018.
Perez et al., Production of four potentially probiotic lactic acid bacteria and their evaluation as feed additives for piglets, Animal Feed Science and Technology, 134:89-107 (2007).
Lin et al., Probiotics as alternative biomedicines for pets with digestive disorders, Proceedings of 8th Annual Meeting of JBVP, p. 288-293 (2006).
Mandal et al., Optimized culture conditions for bacteriocin production by Pediococcus acidilactici LAB 5 and its characterization, Indian Journal of Biochemistry and Biophysics, 45:106-110 (2008).
Furr et al., Orally Administered Pediococcus acidilactici and *Saccharomyces* boulardii—Based Probiotics Alter Select Equine Immune Function Parameters, Journal of Equine Veterinary Science, 34:1156-1163 (2014).
U.S. Office Action from U.S Appl. No. 13/676,579, dated Nov. 12, 2015.
U.S. Office Action from U.S. Appl. No. 13/676,579, dated May 29, 2015.

(Continued)

*Primary Examiner* — Taeyoon Kim
(74) *Attorney, Agent, or Firm* — Nevrivy Patent Law Group P.L.L.C.

(57) ABSTRACT

The present invention provides compositions comprising a probiotc in admixture with an effective amount of an amphipathic substance that enhances viability of the probiotic in the composition when the composition is subjected to heat.

7 Claims, 6 Drawing Sheets

(56) References Cited

OTHER PUBLICATIONS

Abstract of Japanese Pat. No. 2009-514515.
Abstract of Japanese Pat. No. 2013505257.
Abstract of Japanese Pat. No. 62232334.
Abstract of Japanese Pat. No. 2007529214.
Abstract of Japanese Pat. No. 2017012157.
Abstract of Japanese Pat. No. 2003334065.
Abstract of Japanese Pat. No. 104472426. Japanese Office Action from Appl. No. 2018-547873, dated Sep. 24, 2020.
Translation of Japanese Office Action from Appl. No. 2018-547873, dated Sep. 24, 2020.
WebMD. "Malignant Hypertension". Retrieved from: https://www.webmd.com/hypertension-high-blood-pressure/guide/what-is-malignant-hypertension#1 (year: 2019).
Takata, K. et al. 2011. The Lactic Acid Bacterium Pediococcus acidilactici Suppresses Autoimmune Encephalomyelitis by Inducing IL-10-Producing Regulatory T Cells. PLoS One. 6(11): e27644-27651. (Year"2011).
Martinez, F. O. et al. 2014. The M1 and M2 paradigm of macrophage activation: time for reassessment. F1000 Prime Reports. 6(13). (Year: 2014).
Mehta, R. et al. 2013. Bio-preservative and Therapeutic Potential of Pediocin: Recent Trends and Future Perspectives. Recent Patents on Biotechnology. 7: 172-178. (Year: 2013).
Franks, T. 2016. What is Standard Therapy in Cancer Treatment?. Translational Drug Development. Retrieved from: https://www.td2inc.com/news/what-is-standard-therapy-in-cancer-treatment (Year: 2016).
Office Action from U.S. Appl. No. 16/266,397, dated Jun. 23, 2020.

\* cited by examiner

COMPOSITIONS COMPRISING PROBIOTICS AND METHODS OF USE THEREOF

CROSS REFERENCE TO RELATED APPLICATIONS

This application is a continuation-in-part of U.S. application Ser. No. 15/072,308, filed Mar. 16, 2016, which claims the benefit of U.S. Provisional Appl. No. 62/386,347, filed Nov. 30, 2015 and U.S. Provisional Appl. No. 62/177,468, filed Mar. 16, 2015. The content of the aforesaid applications are relied upon and incorporated by reference in their entireties.

FIELD OF THE INVENTION

The field of the invention relates to compositions and uses of probiotics, including *Pediococcus acidilactici* bacteria.

BACKGROUND OF THE INVENTION

Probiotics are beneficial microorganisms naturally existing in gastrointestinal (GI) tracts of humans and animals. In 2001, the World Health Organization defined probiotics as "Live microorganisms, which, when administered in adequate amounts, confer a health benefit on the host" (Joint FAO/WHO Expert Consultation Report, 2001). Many probiotics-related health benefits such as decreasing symptoms from antibiotics-induced diarrhea, acute diarrhea, traveler diarrhea, allergy, respiratory and urinary tract infections, inflammatory bowel disease, irritable bowel syndrome, colon and bladder cancer, and rheumatoid arthritis have been reported. Conventionally, *Bifidobacterium* and *Lactobacillus* are commercially available probiotics. However, these bacteria are sensitive to air exposure, elevated temperature, and stomach acids.

*Pediococcus acidilactici* is a plant based probiotic that is widely applied in sausage preparation for human consumption and as animal feed additives to improve animal health. Moreover, *P. acidilactici* was reported to be able to stimulate the antibody production against parasitic infection of broiler chicken coccidiosis, and ovalbumin antibody production in ovalbumin vaccinated horses (Furr et al., *Journal of Equine Veterinary Science*, 34:1156-1163 (2014)). Both T-cell and B-cell multiplication were detected in rats fed with *Pediococcus*-based probiotics which were mixtures of *P. acidilactici* and *Saccharomyces boulardii*.

One of the challenges of formulating probiotics in food and pharmaceutical/nutraceutical products for administration to subjects is incompatibility with the products and the process of making the products, particularly pasteurization or treatments under harsh conditions such as heat. The harsh conditions can result in a significant loss in viability of the probiotics. The inability to effectively pasteurize the products in the presence of the probiotic without significant loss in viability results in additional processing steps to the manufacturing process, which increases complexity and costs.

Accordingly, there is a need for new compositions and methods comprising probiotics such as *Pediococcus acidilactici*, particularly methods for enhancing the viability of probiotics when subjected to heat.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

According to non-limiting example embodiments, in one aspect, the invention provides a composition comprising a probiotc in admixture with an effective amount of an amphipathic substance that enhances viability of the probiotic in the composition when the composition is subjected to heat.

In another aspect, the invention provides a container suitable for containing a food product comprising a composition comprising a probiotc in admixture with an effective amount of an amphipathic substance that enhances viability of the probiotic in the composition when the composition is subjected to heat.

In another aspect, the invention provides a container suitable for containing a food product, wherein a portion or surface of the container is coated with an effective amount of *Pediococcus acidilactici*.

In another aspect, the invention provides a method of enhancing the viability of a probiotic in a composition that is subjected to heat, comprising
i) adding an effective amount of an amphipathic substance to a composition comprising a probiotic; and
ii) subjecting the composition to heat,
whereby the viability of the probiotic in the composition subjected to the heat has been enhanced.

In another aspect, the invention provides a method of treating a disease or condition characterized by inflammation in a subject in need thereof, comprising administering to the subject an effective amount of a *Pediococcus acidilactici* probiotic composition as described herein.

In some embodiments, the administration of *Pediococcus acidilactici* probiotic increases the number of anti-inflammatory M2 macrophage cells in the subject, thereby treating the disease or condition. In some embodiments, the administration of *Pediococcus acidilactici* probiotic increases IL-10 production in the subject, thereby treating the disease or condition. In some embodiments, the administration of *Pediococcus acidilactici* probiotic decreases the levels of IL-6 and/or IL-23 in the subject, thereby treating the disease or condition.

In some embodiments, the disease or condition characterized by inflammation is selected from the group consisting of malignancy (cancer), arthritis, cardiovascular disease, hepatitis, infection, wound healing, pancreatitis, gastroesophageal reflux disease, diabetes, inflammatory bowel disease, peptic ulcer disease, bronchitis, cholecystitis, appendicitis, bursitis, dermatitis, asthma, autoimmune disease, pelvic inflammatory disease, gout, trauma, foreign body infection, burns, dental work, tendonitis, rhinitis, mucositis, and exposure to toxins such as chemicals and alcohol.

In some embodiments, the *Pediococcus acidilactici* probiotic is strain NRRL B-50517. In some embodiments, the subject is a human.

In some embodiments, the subject is administered greater than $1.0 \times 10^9$ cfu of the probiotic. In some embodiments, the subject is administered greater than $4.0 \times 10^9$ cfu of the probiotic.

In some embodiments, the subject is administered one or more additional therapeutic agents. In some embodiments, the subject is administered one or more chemotherapeutic (anti-cancer) agents and/or radiotherapy in combination with the *Pediococcus acidilactici* probiotic.

In some embodiments, the subject is not administered another therapeutic agent. In some embodiments, the subject is not administered another probiotic.

In another aspect, the invention provides a composition comprising a *Pediococcus acidilactici* probiotic. In some embodiments, the *Pediococcus acidilactici* is strain NRRL B-50517. In some embodiments, the composition is a pharmaceutical composition.

It is to be understood that both the foregoing general description and the following detailed description are exemplary, and thus do not restrict the scope of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

Figure 1:
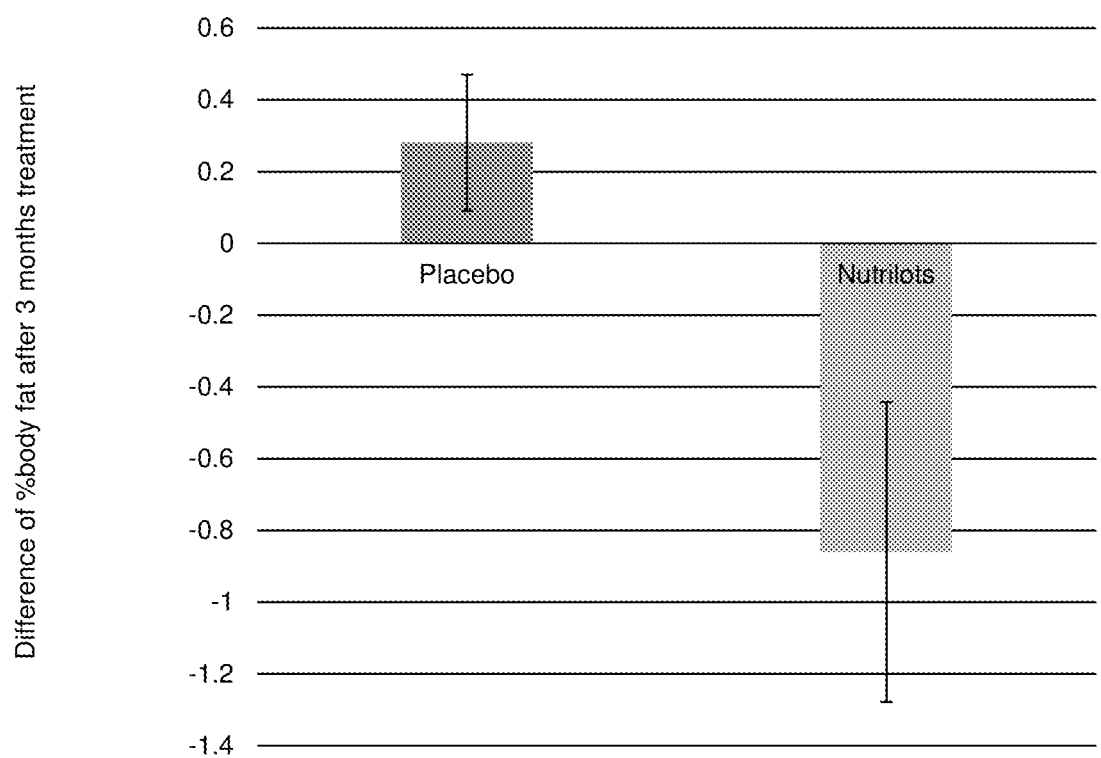
FIG. 1. Effect of *P. acidilactici* 5051 probiotic on body fat %.

The invention is based, in part, on the surprising discovery that the viability of probiotics such as *Pediococcus acidilactici* can be enhanced when combined with effective amounts of an amphipathic substance when the composition is subjected to heat. The invention is also based, in part, on the surprising discovery that administration of effective amounts of a *Pediococcus acidilactici* probiotic are able to treat diseases or conditions characterized by inflammation.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of" As used herein, the term "about" means at most plus or minus 10% of the numerical value of the number with which it is being used.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

Heat Resistant Probiotic Compositions and Methods of Making

In one embodiment, the invention provides a composition comprising a probiotic in admixture with an effective amount of an amphipathic substance that enhances viability of the probiotic in the composition when the composition is subjected to heat. The composition comprises an effective amount of a probiotic when suitable for administration to a subject.

In another embodiment, the invention comprises a method of making a probiotic composition with improved viability in response to heat, comprising adding an effective amount of an amphipathic substance to a composition comprising a probiotic.

In another embodiment, the invention comprises a method of enhancing the viability of a probiotic in a composition that is subjected to heat, comprising i) adding an effective amount of an amphipathic substance to a composition comprising a probiotic; and
ii) subjecting the composition to heat,
whereby the viability of the probiotic in the composition subjected to the heat has been enhanced.

The probiotic is not particularly limiting. In some embodiments, the probiotic is mixed with the amphipathic substance as a freeze dried fermentive culture. In some embodiments, the probiotic is *Pediococcus acidilactici*. The *Pediococcus acidilactici* probiotic that can be used in accordance with the invention is not limiting. In some embodiments, the *Pediococcus acidilactici* is a strain that is viable above 65° C., is able to grow in aerobic and anaerobic conditions, and in a pH range between 1 and 6.2. In some embodiments, the *Pediococcus acidilactici* is a strain deposited in the Agricultural Research Service (ARS) Patent Culture Collection as NRRL B-50517. Strain NRRL B-50517 is described in U.S. application Ser. No. 13/676,579, which is herein incorporated by reference.

In some embodiments, the *Pediococcus acidilactici* for use in the invention can be selected for tolerance to elevated temperatures, low pH values, and aerobic and anaerobic conditions.

In some embodiments, the compositions comprise greater than about $1.0 \times 10^9$ cfu of the probiotic. In some embodiments, the compositions comprise greater than $4.0 \times 10^9$ cfu of the probiotic.

Amphipathic molecules are molecules having both polar and non-polar portions in their structure. Amphipathic molecules generally have a hydrophobic portion of the molecule that orients into a hydrophobic phase and a hydrophilic portion that orients toward the aqueous phase.

Some of the chemical compounds that feature these molecules are essential to a host of biological and industrial processes. In some embodiments, the amphipathic substance comprises lecithin, peanut butters, almond butters, soy butters or cookie butter as carriers of the probiotic such as *Pediococcus acidilactici* NRRL B-50517 fermentative cultures. In some embodiments, excess amounts of amphipathic substances are used and can protect *P. acidilactici* NRRL B-50517 fermentative cultures from harsh dry heat or wet heat treatment. Lethicin is a phosphatidylcholine and can comprise natural mixtures of neutral and polar lipids from vegetable and/or animal sources. It has low solubility in water, but is an excellent emulsifier. In aqueous solution, its phospholipids can form either liposomes, bilayer sheets, micelles, or lamellar structures, depending on hydration and temperature. This results in a type of surfactant that usually is classified as amphipathic.

In some embodiments the amphipathic substance is a lipid. Hydrophilic characteristics derive from the presence of polar or charged groups such as carbohydrates, phosphato, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and β-acyloxyacids, are also within the group designated as amphipathic lipids.

In some embodiments, the amphipathic substance comprises lecithin, peanut butter, almond butter, soy butter or cookie butter. In some embodiments, the amphipathic substance is sunflower lecithin.

An "effective amount" of an amphipathic substance as described herein is an amount that is capable of enhancing the viability of the probiotic in response to heat, as compared with the viability of the probiotic in the absence of the amphipathic substance. In some embodiments, the viability of the probiotic is enhanced at least about 2-fold compared with a composition that lacks the effective amount of amphipathic substance. In some embodiments, viability is enhanced at least about 25%, 50%, 75%, 2-fold, 3-fold, 4-fold, 5-fold, 6-fold, 7-fold, 8-fold, 9-fold or 10-fold. In some embodiments, viability is enhanced at least about 10-fold compared with a composition that lacks the effective amount of amphipathic substance.

In some embodiments, the ratio (w/w) of the amphipathic substance to the probiotic ranges from about 1:10 to about 25:1. In some embodiments, the ratio (w/w) of the amphipathic substance to the probiotic ranges from about 1:1 to about 10:1. In some embodiments, the ratio (w/w) of the amphipathic substance to the probiotic is about 5:1. In some embodiments, the ratio (w/w) of the amphipathic substance to the probiotic is about 10:1. In some embodiments, the ratio of the amphipathic substance can be higher than 25:1. For example, in some embodiments, the peanut butter powders and/or lecithin can be treated as sugar carriers. In some embodiments, up to 1 part of probiotics to 25 parts of lecithin or peanut butter can be produced, but it can be as high as one would like to blend probiotics with sugar carriers. This means, one part probiotics can mix with 100 parts (or even higher) of lecithin or peanut butter powders without problems.

In some embodiments, the amphipathic substance is mixed with the probiotic as a dried powder. In some embodiments, the amphipathic substance serves as a carrier and can be combined with the probiotic and an oil, forming a lipid paste that makes the probiotic more resistant to heat, such as dry heat treatment or liquid heat treatment, such as pasteurization processes for food treatment. The oil is not particularly limiting and can include edible oils. In some embodiments, the oil can include oils from plant sources such as olive oil, palm oil, soybean oil, fish oil, sunflower oil, canola oil (rapeseed oil), corn oil, peanut oil and other vegetable oils, as well as animal-based oils like butter and lard. In some embodiments, the oil is olive oil. In some embodiments, the ratio (w/w) of the amphipathic substance to the probiotic and to the oil ranges from about 1:10:0.1 to about 10:1:25. In some embodiments, the ratio (w/w) of the amphipathic substance to the oil is from about 1:0.5 to about 0.5:1. In some embodiments the ratio (w/w) of the amphipathic substance to the oil is about 1:1.

The nature of the heat is not necessarily limiting, and can include dry heat, water vapor and liquid heat treatment. Liquid heat means the product is submerged into the hot liquid such as water and the heat treatment is performed together with the liquid.

In some embodiments, the composition is subjected to a dry heat. Dry heat treatment can be accomplished using an oven or hot plate without water and water vapors. In some embodiments, the heating can start at a first temperature and ending at a second, desired temperature. In some embodiments, the composition is subjected immediately to dry heat at the desired temperature without a heating step. In some embodiments, the desired temperature of the dry heat is at least 50° C. In some embodiments, the dry heat is at least about 50° C., 51° C., 52° C., 53° C., 54° C., 55° C., 56° C., 57° C., 58° C., 59° C., 60° C., 61° C., 62° C., 63° C., 64° C., 65° C., 70° C., 75° C., 80° C., 85° C., 90° C., 95° C. of 100° C. In some embodiments, the dry heat ranges from 65-100° C. The composition can also be subjected to dry heat at a first temperature for a period of time, and then exposed one or more heat treatments at one or more different temperatures for a period of time.

The duration of exposure to the heat is not particularly limiting. In some embodiments, the composition is exposed to heat instantly, and then immediately removed from heat. In some embodiments, the composition is subjected to heat for at least about 1 second. In some embodiments, the composition is subjected to heat for at least about 1 second, 2 seconds, seconds, 4 seconds, 5 seconds, 6 seconds, 7 seconds, 8 seconds, 9 seconds, 10 seconds, 20 seconds, 30 seconds, 40 seconds, 50 seconds, 1 minute, 2 minutes, 3 minute, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, or at least two hours. In some embodiments, the composition is subjected to heat for at least about 10 minutes. In some embodiments, the composition is subjected to dry heat at a first temperature, followed by subjecting the composition to dry heat at a second temperature. In some embodiments, the first temperature is about 50-65° C. and the second temperature is about 85° C. or higher. In some embodiments, the composition is subjected to heat at the first temperature for at least about 1 second to at least about 2 hours and is subjected to heat at the second temperature for at least about 1 second to at least about 2 hours. In some embodiments, the composition is subjected to the first temperature overnight. In some embodiments, the composition is subjected to the second temperature overnight. In some embodiments, the composition is subjected to heat at the first temperature for about 30 minutes and is subjected to heat at the second temperature for about 10 minutes. In some embodiments, the composition is subjected to heat at the first temperature for about 30 minutes and is subjected to heat at the second temperature for about 30 minutes. In some embodiments, the purpose of the multiple heat treatments at different temperatures is to make sure that samples are at the right temperature for the second temperature treatment, because it can take some time for materials to heat from room temperature to, e.g., 85° C. In some embodiments, the compositions are pretreated at 65° C. for 30 minutes to overnight and then shifted to 85° C. for the treatment time to achieve the right temperature heat treatment.

In some embodiments, the composition is subjected to liquid heat. In some embodiments, the liquid heat is at least about 50° C., 51° C., 52° C., 53° C., 54° C., 55° C., 56° C., 57° C., 58° C., 59° C., 60° C., 61° C., 62° C., 63° C., 64° C., 65° C., 70° C., 75° C., 80° C., 85° C., 90° C., or 95° C. In some embodiments, the liquid heat is at least about 50-65° C. In some embodiments, the liquid heat ranges from about 65° C. to about 95° C. In some embodiments, the liquid heat is at least about 70° C., 75° C., or 80° C. In some embodiments, the liquid heat is at least about 81° C., 82° C., 83° C., 84° C. 85° C., 86° C., 87° C., 88° C., 89° C., 90° C., 91° C., 92° C., 93° C., 94° C., or 95° C.

In some embodiments, the composition is exposed to liquid heat instantly, and then immediately removed from heat. In some embodiments, the composition is subjected to the liquid heat for at least about one second. In some embodiments, the composition is subjected to the liquid heat for at least about one second to about one hour. In some embodiments, the composition is subjected to the liquid heat for at least about 1 second, 2 seconds, seconds, 4 seconds, 5 seconds, 6 seconds, 7 seconds, 8 seconds, 9 seconds, 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, or at least one hour. In some embodiments, the composition is subjected to the heat for at least about 5 minutes. In some embodiments, the composition is subjected to the heat for at least about 10 minutes.

In some embodiments, the composition is contacted with a food, pharmaceutical, or nutraceutical product and subjected to heat together with the product. In some embodiments, an already heated food, pharmaceutical, or nutraceutical product is dispensed into a container comprising the composition or otherwise combined with the composition. In some embodiments, the already heated food, pharmaceutical, or nutraceutical product is contacted very shortly after the heat treatment, without a significant cooling step prior to combining the product with the probiotic composition. Thus, in some embodiments, the subjecting the composition to a heat step of part ii) comprises contacting the composition with a food, pharmaceutical, or nutraceutical product, wherein the food, pharmaceutical, or nutraceutical product had been previously subjected to heat prior to contacting the composition. In some embodiments, the composition will be present within a container that the heated food, pharmaceutical, or nutraceutical product is dispensed into.

Containers

In some embodiments, the invention further provides a container suitable for containing a food, pharmaceutical, or nutraceutical product comprising compositions as described herein. In some embodiments, the container is made from a substance comprising glass, plastic, paper/carton, aluminum or dried plant fruit shell. The composition and shape of the container is not limiting provided that it is suitable for containing a food, pharmaceutical or nutraceutical product. In some embodiments, the container is coated with a probiotic composition as described herein.

In some embodiments, the container is coated with an effective amount of *Pediococcus acidilactici*. In some embodiments the *Pediococcus acidilactici* is strain NRRL B-50517. In some embodiments, a composition comprising a probiotic such as *Pediococcus acidilactici*, including strain NRRL B-50517 and an amphipathic substance such as sunflower lecithin as provided herein is coated onto a surface or portion of the container. In some embodiments, the container further comprises a food, nutraceutical or pharmaceutical product. In some embodiments, the food product comprises oil, vinegar, yogurt, fruit product, applesauce, dairy product, beverage, candy, snack items, juice or food for deserts such as cookies, cake, JELLO, fruit bars, fruit custard, or tiramisu. In some embodiments, a heated food, nutraceutical or pharmaceutical product is dispensed into the coated container, followed by sealing of the container.

Methods of Treatment

According to non-limiting example embodiments, in one aspect, the invention provides a method of treating a disease or condition characterized by inflammation in a subject in need thereof, comprising administering to the subject an effective amount of a *Pediococcus acidilactici* probiotic. In some embodiments, the subject is administered a composition as described herein. In some embodiments, the composition comprises a probiotic and amphipathic substance as described herein.

As used herein, "treat" and all its forms and tenses (including, for example, treating, treated, and treatment) refers to therapeutic treatment. In certain aspects of the invention, those in need of treatment include those already with a pathological disease or condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the disease or pathological condition.

The subject to be treated herein is not limiting. In some embodiments, the subject to be treated is a mammal, bird, reptile or fish. Mammals that can be treated in accordance with the invention, include, but are not limited to, humans, dogs, cats, horses, mice, rats, guinea pigs, sheep, cows, pigs, monkeys, apes and the like, subject to a disease or other pathological condition characterized by inflammation. The term "patient" and "subject" are used interchangeably. In some embodiments, the subject is a human.

The *Pediococcus acidilactici* probiotic can be administered 1, 2, 3, 4, 5, 6, 7, 8, 9, 10, 11, or 12 times per day. In some embodiments, the *Pediococcus acidilactici* probiotic is administered 4 times a day, 2 times a day, or once per day. In some embodiments, the *Pediococcus acidilactici* probiotic is administered every 2 hours, every 4 hours, every six hours, every 8 hours, every 10 hours, every 12 hours or every 24 hours. In some embodiments, the *Pediococcus acidilactici* probiotic is administered once a day.

The duration of administration of the *Pediococcus acidilactici* probiotic can vary for each individual to be treated/administered depending on the individual cases and the diseases or conditions to be treated. In some embodiments, the *Pediococcus acidilactici* probiotic can be administered continuously for a period of several days, weeks, months, or years of treatment or can be intermittently administered where the individual is administered the *Pediococcus acidilactici* probiotic for a period of time, followed by a period of time where they are not treated, and then a period of time where treatment resumes as needed to treat the disease or condition. For example, in some embodiments, the individual to be treated is administered the *Pediococcus acidilactici* probiotic of the invention daily, every other day, every three days, every four days, 2 days per week 3 days per week, 4 days per week, 5 days per week or 7 days per week. In some embodiments, the individual is administered the *Pediococcus acidilactici* probiotic for 1 week, 2 weeks, 3 weeks, 4 weeks, 1 month, 2 months, 3 months, 4 months, 5 months, 6 months, 7 months, 8 months, 9 months, 10 months, 11 months, 1 year or longer.

In some embodiments, the administration of *Pediococcus acidilactici* probiotic increases the number of anti-inflammatory M2 macrophage cells in the subject, thereby treating the disease or condition. In some embodiments, the anti-inflammatory M2 macrophage cells increase by about 10%, about 20%, about 30%, about 40%, about 50%, about 60%, about 70%, about 80%, about 90%, about 100%, about 125%, about 150%, about 175%, about 200%, about 250%, about 300%, about 350%, about 400%, or about 450%, about 500%, about 600%, about 700%, about 800%, about 900% or about 1000% or more over untreated levels.

In some embodiments, the administration of *Pediococcus acidilactici* probiotic increases IL-10 production in the subject, thereby treating the disease or condition. In some embodiments, the IL-10 production increases by about 10%, about 20%, about 30%, about 40%, about 50%, about 60%, about 70%, about 80%, about 90%, about 100%, about 125%, about 150%, about 175%, about 200%, about 250%, about 300%, about 350%, about 400%, or about 450%, about 500%, about 600%, about 700%, about 800%, about 900% or about 1000% or more over untreated levels.

In some embodiments, the administration of *Pediococcus acidilactici* probiotic decreases the levels of IL-6 and/or IL-23 in the subject, thereby treating the disease or condition. In some embodiments, the levels of IL-6 and/or IL-23 decrease by about 10%, about 20%, about 30%, about 40%, about 50%, about 60%, about 70%, about 80%, about 90%, or about 100% over untreated levels.

In some embodiments, the administration of *Pediococcus acidilactici* probiotic increases the number of anti-inflammatory M2 macrophage cells in the subject, in combination with increasing IL-10 production, and optionally decreasing IL-6 and/or IL-23 in the subject.

In some embodiments, the disease or condition characterized by inflammation is selected from the group consisting of malignancy (cancer), arthritis, cardiovascular disease, hepatitis, infection, wound healing, pancreatitis, gastroesophageal reflux disease, diabetes, inflammatory bowel disease, peptic ulcer disease, bronchitis, cholecystitis, appendicitis, bursitis, dermatitis, asthma, autoimmune disease, pelvic inflammatory disease, gout, trauma, foreign body infection, burns, dental work, tendonitis, rhinitis, mucositis, and exposure to toxins such as chemicals and alcohol.

As used herein, "cancer" refers to a pathophysiological condition whereby cells are characterized by dysregulated and/or proliferative cellular growth and the ability to induce said growth, which includes but is not limited to, carcinomas and sarcomas, such as, for example, acute lymphoblastic leukemia, acute myeloid leukemia, adrenocortical cancer, AIDS-related cancers, AIDS-related lymphoma, anal cancer, astrocytoma (including, for example, cerebellar and cerebral), basal cell carcinoma, bile duct cancer, bladder cancer, bone cancer, brain stem glioma, brain tumor (including, for example, ependymoma, medulloblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (including, for example, gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (including, for example, intraocular melanoma, retinoblastoma, gallbladder cancer, gastric cancer, gastrointestinal carcinoid tumor, gastrointestinal stromal tumor (GIST), germ cell tumor (including, for example, extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (including, for example, endocrine pancreas), Kaposi's sarcoma, laryngeal cancer, leukemia, lip and oral cavity cancer, liver cancer, lung cancer (including, for example, non-small cell), lymphoma, macroglubulinemia, malignant fibrous histiocytoma of bone/osteosarcoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplasia syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (including, for example, ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sezary syndrome, skin cancer (including, for example, non-melanoma or melanoma), small intestine cancer, supratentorial primitive neuroectodermal tumors, T-Cell lymphoma, testicular cancer, throat cancer, thymoma, thymoma and thymic carcinoma, thyroid cancer, transitional cell cancer of the renal pelvis and ureter, trophoblastic tumor (including, for example, gestational), unusual cancers of childhood and adulthood, urethral cancer, endometrial uterine cancer, uterine sarcoma, vaginal cancer, viral induced cancers (including, for example, HPV induced cancer), vulvar cancer, Waldenstrom's macroglobulinemia, Wilms' Tumor, and women's cancers.

The *Pediococcus acidilactici* probiotic that can be used in accordance with the invention is not limiting. In some embodiments, the *Pediococcus acidilactici* is a strain that is viable above 65° C., is able to grow in aerobic and anaerobic conditions, and in a pH range between 1 and 6.2. In some embodiments, the *Pediococcus acidilactici* is a strain deposited in the Agricultural Research Service (ARS) Patent Culture Collection as NRRL B-50517. Strain NRRL B-50517 is described in U.S. application Ser. No. 13/676,579, which is herein incorporated by reference.

In some embodiments, the *Pediococcus acidilactici* for use in the invention can be selected for tolerance to elevated temperatures, low pH values, and aerobic and anaerobic conditions.

In accordance with the treatment methods of the invention, a "therapeutically effective amount" or "effective amount" is administered to the subject. As used herein a "therapeutically effective amount" or "effective amount" is an amount sufficient to decrease, suppress, or ameliorate one or more symptoms associated with the disease or condition. In some embodiments, the subject is administered greater than $1.0 \times 10^9$ cfu of the probiotic. In some embodiments, the subject is administered greater than $4.0 \times 10^9$ cfu of the probiotic.

In some embodiments, the subject is administered one or more additional therapeutic agents. In some embodiments, the one or more additional therapeutic agents are those commonly used to treat the disease or condition characterized by inflammation.

In some embodiments, the subject is administered in combination an anti-inflammatory drug. In some embodiments, the administered *Pediococcus acidilactici* and anti-inflammatory drug act synergistically. In some embodiments, the anti-inflammatory drug is a non-steroidal anti-inflammatory drug (NSAID). In some embodiments, anti-inflammatory drug is selected from the group consisting of Antazoline, Balsalazide, Beclometasone, Betamethasone, Budesonide, Celecoxib, Colchicine, Deflazacort, Dexamethasone, Dexibuprofen, Diclofenac, Etanercept, Etodolac, Felbinac, Fenoprofen, Flumetasone, Fluorometholone, Flurbiprofen, Flurbiprofen, Fluticasone, Gentamicin, Hydrocortisone, Ibuprofen, Indometacin, Ketoprofen, Loteprednol, Mefenamic acid, Meloxicam, Mesalazine, Methylprednisolone, Mometasone, Nabumetone, Naproxen, Nepafenac, Olsalazine, Prednisolone, Rimexolone, Sulfasalazine, Sulindac, Tenoxicam, Tiaprofenic acid, Triamcinolone and combinations thereof.

In some embodiments, the subject is administered one or more anti-cancer agents and/or radiotherapy in combination with the *Pediococcus acidilactici* probiotic to treat cancer in the subject.

In some embodiments, the anti-cancer agent is selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Di sodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate). In some embodiments, the drug is selected from the group consisting of Paclitaxel, Curcumin, Docetaxel, Ixabepilone, Vinblastine, Colchicine, Y-27632 Fasudil, SU6656 Dasatinib, HDAC inhibitors, ROCK inhibitors, Parthenolide, Costunolide and ML-7 Jazplakinolide.

In some embodiments, the subject is not administered another therapeutic agent and is administered a composition consisting of or consisting essentially of the *Pediococcus acidilactici* probiotic, optionally in admixture with an amphipathic substance and/or food.

In some embodiments, the subject is administered one or more additional probiotics. In some embodiments, the subject is not administered another probiotic.

Compositions

In some embodiments, the invention provides a composition comprising a *Pediococcus acidilactici* probiotic. In some embodiments, the composition comprises *Pediococcus acidilactici* NRRL B-50517. In some embodiments, the compositions comprise effective amounts of *Pediococcus acidilactici*, including *Pediococcus acidilactici* NRRL B-50517. In some embodiments, the invention provides a composition comprising a *Pediococcus acidilactici* probiotic in admixture with an effective amount of an amphipathic substance and optionally an oil as described herein. In some embodiments, the composition comprises a food, pharmaceutical or nutraceutical product in combination with *Pediococcus acidilactici* probiotic in admixture with an effective amount of an amphipathic substance and optionally an oil.

In some embodiments the compositions are pharmaceutical compositions. In some embodiments, the compositions are pharmaceutical compositions comprising effective amounts of *Pediococcus acidilactici*, including *Pediococcus acidilactici* NRRL B-50517 which are capable of treating of one or more diseases or conditions characterized by inflammation. In some embodiments, the compositions are pharmaceutical compositions comprising effective amounts of *Pediococcus acidilactici*, including *Pediococcus acidilactici* NRRL B-50517 in admixture with an effective amount of an amphipathic substance and optionally an oil and which are capable of treating of one or more diseases or conditions characterized by inflammation.

In some embodiments, the pharmaceutical composition comprises one or more pharmaceutically acceptable carriers or excipients. Pharmaceutically acceptable carriers and excipients are those that are compatible with the other ingredients in the formulation and biologically acceptable. The *Pediococcus acidilactici* can be provided in combination with a pharmaceutically acceptable carrier, excipients or diluent. Suitable carriers, excipients and/or diluents include, but are not limited to, pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration). The *Pediococcus acidilactici* can also be administered in sachets that have to be added to a glass of water and then drunk.

In some embodiments, the composition is suitable for oral administration. In some embodiments, the composition is a tablet, capsule, pill, dragee, suspension, lozenge, emulsion, aqueous solution, liquid, gel, or syrup. In some embodiments, the compositions can be delivered in the form of functional foods and/or beverages, as well as in the form of various supplements.

Formulations of the present invention suitable for oral administration may be presented as discrete units such as capsules, cachets or tablets each containing a predetermined amount of the *Pediococcus acidilactici*; as a powder or granules, which in some embodiments can be wettable, spray-dried or freeze-dried; as a solution or a suspension in an aqueous or non-aqueous liquid; or as an oil-in-water liquid emulsion or a water-in-oil liquid emulsion.

In some embodiments, a tablet can be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

In some embodiments, the composition comprises one or more of the following: tablets, pills, capsules, ovules, solutions or suspensions, which may contain flavouring or colouring agents, for immediate-, delayed-, modified-, sustained-, pulsed- or controlled-release applications.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

In some embodiments, the compositions of the invention are formulated in unit dosage form for ease of administration and uniformity of dosage. The term "unit dosage form" as used herein refers to physically discrete units suited as unitary dosages for the individuals to be treated. In some embodiments, the compositions are formulated into discrete dosage units each containing a predetermined "unit dosage" or "unit dose" of one or more active compounds calculated to produce the desired effect in association with the required pharmaceutical carrier.

In some embodiments, the composition comprises gelatin capsules. In some embodiments, the gelatin capsules comprise effective amounts of *P. acidilactici* NRRL B-50517 fermentative cultures with peach fruit powder, in a dose of from about 1-4 billion CFU.

While is it possible to administer *Pediococcus acidilactici* alone according to the present invention, the *Pediococcus acidilactici* are typically administered on or in a support as part of a product, in particular as a component of a food product, a dietary supplement or a pharmaceutical formulation. These products typically contain additional components well known to those skilled in the art. In one embodiment, the composition comprises a *Pediococcus acidilactici* probiotic in admixture with an effective amount of an amphipathic substance and optionally an oil.

In one embodiment, the *Pediococcus acidilactici* are employed according to the invention in a food product such as a food supplement, a drink or a powder based on milk. Here, the term "food" is used in a broad sense—and covers food for humans as well as food for animals (i.e. a feed). In one embodiment, the food is for human consumption.

The food may be in the form of a solution or as a solid, depending on the use and/or the mode of application and/or the mode of administration.

When used as, or in the preparation of, a food, such as functional food, the compositions of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the composition of the present invention can be used as an ingredient to soft drinks, a fruit juice or a beverage comprising whey protein, health teas, cocoa drinks, milk drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped topping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

The term "dairy product" as used herein is meant to include a medium comprising milk of animal and/or vegetable origin. As milk of animal origin there can be mentioned cow's, sheep's, goat's or buffalo's milk. As milk of vegetable origin there can be mentioned any fermentable substance of vegetable origin which can be used according to the invention, in particular originating from soybeans, rice or cereals.

In some embodiments, the food product employed according to the invention is a fermented milk or humanized milk.

In some embodiments, the compositions can be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing a composition according to the present invention with another food ingredient.

In some embodiments, the present invention relates to products that have been contacted with the composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is preferably admixed with the product. Alternatively, the composition may be included in the emulsion or raw ingredients of a foodstuff. In a further alternative, the composition may be applied as a seasoning, glaze, colorant mixture, and the like.

For some applications, it is important that the composition is made available on or to the surface of a product to be affected/treated. This allows the composition to impart one or more of the following favourable characteristics: nutrition and/or health benefits.

The compositions of the present invention may be applied to intersperse, coat and/or impregnate a product with a controlled amount of a viable microorganism.

In some embodiments, the composition is used to ferment milk or sucrose fortified milk or lactic media with sucrose and/or maltose where the resulting media containing all components of the composition—i.e. said microorganism according to the present invention—can be added as an ingredient to yoghurt milk in suitable concentrations—such as for example in concentrations in the final product which offer a daily dose of $10^6$–$10^{10}$ cfu. The microorganism according to the present invention may be used before or after fermentation of the yoghurt.

In some aspects, the microorganisms according to the present invention are used as, or in the preparation of, animal feeds, such as livestock feeds, in particular poultry (such as chicken) feed, pet food, or pet treats.

In some embodiments, where the product is a food product, the *Pediococcus acidilactici* should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognize that shelf-life times will vary upon the type of foodstuff, the size of the foodstuff, storage temperatures, processing conditions, packaging material and packaging equipment.

In some embodiments, the composition of the present invention may be used as a food ingredient and/or feed ingredient. As used herein the term "food ingredient" or "feed ingredient" includes a formulation which is or can be added to functional foods or foodstuffs as a nutritional supplement. The food ingredient may be in the form of a solution or as a solid—depending on the use and/or the mode of application and/or the mode of administration.

In some embodiments, the composition of the present invention may be—or may be added to—food supplements (also referred to herein as dietary supplements).

In some embodiments, the composition of the present invention may be—or may be added to—functional foods. As used herein, the term "functional food" means food which is capable of providing not only a nutritional effect, but is also capable of delivering a further beneficial effect to consumer. Accordingly, functional foods are ordinary foods that have components or ingredients (such as those described herein) incorporated into them that impart to the food a specific functional—e.g. medical or physiological benefit—other than a purely nutritional effect. Although there is no legal definition of a functional food, most of the parties with an interest in this area agree that they are foods marketed as having specific health effects beyond basic nutritional effects. Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

In some embodiments, the invention provides a composition comprising *Pediococcus acidilactici* such as *Pedio-

*coccus acidilactici* NRRL B-50517 and an edible oil. In some embodiments, the edible oil is selected from the group consisting of olive oil, corn oil, EVOO, LTOO, peanut oil, and vegetable oil. In some embodiments, the ratio (w/w) of oil to probiotic in the composition ranges from 1:1 to 10:1. In some embodiments, the probiotics exhibit heat resistance in the oil composition.

In some embodiments, the invention provides a composition comprising a sugar such as sucrose or lactose in combination with *Pediococcus acidilactici* such as *Pediococcus acidilactici* NRRL B-50517. In some embodiments, the concentration of the sugar ranges from 0.1% to 50% of the solution.

In some embodiments, the invention provides a composition comprising a salt solution such as NaCl in combination with *Pediococcus acidilactici* such as *Pediococcus acidilactici* NRRL B-50517. In some embodiments, the concentration of the salt ranges from 0.1% to 20% of the solution.

In some embodiments, the invention provides a composition comprising peanut butter in combination with *Pediococcus acidilactici* such as *Pediococcus acidilactici* NRRL B-50517. In some embodiments, the ratio (w/w) of the peanut butter to the probiotic ranges from 1:1 to 10:1.

Sample Embodiments

This section describes exemplary compositions and methods of the invention, presented without limitation, as a series of paragraphs, some or all of which may be alphanumerically designated for clarity and efficiency. Each of these paragraphs can be combined with one or more other paragraphs, and/or with disclosure from elsewhere in this application, including the materials incorporated by reference, in any suitable manner. Some of the paragraphs below expressly refer to and further limit other paragraphs, providing without limitation examples of some of the suitable combinations.

1. A composition comprising an effective amount of a probiotc in admixture with an effective amount of an amphipathic substance that enhances viability of the probiotic in the composition when the composition is subjected to heat.
2. The composition of paragraph 1, wherein the probiotic is mixed with the amphipathic substance as a freeze dried fermentive culture.
3. The composition of any of paragraphs 1-2, wherein the amphipathic substance is mixed with the probiotic as a dried powder.
4. The composition of any of paragraphs 1-3, further comprising an oil that is mixed with the amphipathic substance and probiotic.
5. The composition of paragraph 4, wherein the oil is olive oil.
6. The composition of any of paragraphs 4-6, wherein the ratio (w/w) of the amphipathic substance to the probiotic and to the oil ranges from about 1:10:0.1 to about 10:1:25.
7. The composition of any of paragraphs 1-6, wherein the amphipathic substance forms a lipid paste and serves as a carrier.
8. The composition of any of paragraphs 1-7, wherein the probiotic is *Pediococcus acidilactici*.
9. The composition of any of paragraphs 1-8, wherein the probiotic is *Pediococcus acidilactici* NRRL B-50517.
10. The composition of any of paragraphs 1-9, wherein the amphipathic substance comprises lecithin, peanut butter, almond butter, soy butter or cookie butter.
11. The composition of any of paragraphs 1-10, wherein the heat is dry heat.
12. The composition of paragraph 11, wherein the dry heat is at least 65° C.
13. The composition of any of paragraphs 11-12, wherein the dry heat ranges from 65-95° C.
14. The composition of any of paragraphs 1-13, wherein the composition is subjected to heat for at least 1 second.
15. The composition of any of paragraphs 1-14, wherein the composition is subjected to heat for at least about 10 minutes.
16. The composition of any of paragraphs 1-15, wherein the composition is subjected to dry heat at a first temperature, followed by subjecting the composition to dry heat at a second temperature.
17. The composition of paragraph 16, wherein the first temperature is about 65° C. and the second temperature is about 85° C.
18. The composition of any of paragraphs 16-17, wherein the composition is subjected to heat at the first temperature for at least about 1 second to at least about 30 minutes and is subjected to heat at the second temperature for at least about 1 second to at least about 30 minutes.
19. The composition of any of paragraphs 16-17, wherein the composition is subjected to heat at the first temperature for about 30 minutes and is subjected to heat at the second temperature for about 10 minutes.
20. The composition of any of paragraphs 16-17, wherein the composition is subjected to heat at the first temperature for about 30 minutes and is subjected to heat at the second temperature for about 30 minutes.
21. The composition of any of paragraphs 1-10, wherein the heat is liquid heat.
22. The composition of paragraph 21, wherein the liquid heat is at least about 65° C.
23. The composition of paragraph 21, wherein the liquid heat is at least about 80° C.
24. The composition of paragraph 21, wherein the liquid heat is at least about 82° C.
25. The composition of any of paragraphs 21-24, wherein the composition is subjected to the liquid heat for at least about one second.
26. The composition of any of paragraphs 21-24, wherein the composition is subjected to the heat for at least about 5 minutes.
27. The composition of any of paragraphs 21-24, wherein the composition is subjected to the heat for at least about 10 minutes.
28. The composition of any of paragraphs 1-27, wherein the viability is enhanced at least about 2-fold compared with a composition that lacks the effective amount of amphipathic substance.
29. The composition of any of paragraphs 1-27, wherein the viability is enhanced at least about 10-fold compared with a composition that lacks the effective amount of amphipathic substance.
30. The composition of any of paragraphs 1-29, wherein the amphipathic substance is sunflower lecithin.
31. The composition of any of paragraphs 1-30, wherein the ratio (w/w) of the amphipathic substance to the probiotic ranges from about 1:10 to about 25:1.
32. The composition of any of paragraphs 1-31, wherein the ratio (w/w) of the amphipathic substance to the probiotic ranges from about 1:1 to about 10:1.
33. The composition of any of paragraphs 1-32, wherein the ratio (w/w) of the amphipathic substance to the probiotic is about 5:1.

34. The composition of any of paragraphs 1-32, wherein the ratio (w/w) of the amphipathic substance to the probiotic is about 10:1.

35. A container suitable for containing a food product comprising the composition of any of paragraphs 1-34.

36. The container of paragraph 35, wherein the container is made from a substance comprising glass, plastic, paper/carton, or aluminum.

37. The container of any of paragraphs 35-36, wherein the composition is coated onto a surface or portion of the container.

38. The container of any of paragraphs 35-37, further comprising a food product.

39. The container of paragraph 38, wherein the food product comprises oil, vinegar, yogurt, fruit product, applesauce, dairy product, beverage, candy, snack items, and juice.

40. A container suitable for containing food, wherein a portion or surface of the container is coated with an effective amount of *Pediococcus acidilactici*.

41. The container of paragraph 40, wherein the *Pediococcus acidilactici* is strain NRRL B-50517.

42. The container of any of paragraphs 40 or 41, wherein the container is made from a substance comprising glass, plastic, paper/carton, and aluminum.

43. The container of any of paragraphs 40-43, wherein the *Pediococcus acidilactici* is coated onto an inner surface of the container.

44. The container of any of paragraphs 40-43, further comprising a food product.

45. The container of paragraph 44, wherein the food product comprises oil, vinegar, yogurt, fruit product, applesauce, dairy product, beverage, candy, snack items, and juice.

46. A method of enhancing the viability of a probiotic in a composition that is subjected to heat, comprising
iii) adding an effective amount of an amphipathic substance to a composition comprising a probiotic; and
iv) subjecting the composition to heat,
whereby the viability of the probiotic in the composition subjected to the heat has been enhanced.

47. The method of paragraph 46, wherein the amphipathic substance is mixed with a freeze dried fermentive culture of the probiotic.

48. The method of any of paragraphs 46-47, wherein the amphipathic substance is in the form of a dried powder.

49. The method of any of paragraphs 46-48, wherein the amphipathic substance is mixed with the probiotic and an oil.

50. The method of paragraph 49, wherein the oil is olive oil.

51. The method of any of paragraphs 49-50, wherein the ratio (w/w) of the amphipathic substance to the probiotic and to the oil ranges from about 1:10:0.1 to about 10:1:25.

52. The method of any of paragraphs 46-50, wherein the amphipathic substance forms a lipid paste and serves as a carrier.

53. The method of any of paragraphs 46-52, wherein the probiotic is *Pediococcus acidilactici*.

54. The method of paragraph 2, wherein the probiotic is *Pediococcus acidilactici* NRRL B-50517.

55. The method of any of paragraphs 46-54, wherein the amphipathic substance comprises lecithin, peanut butter, almond butter, soy butter or cookie butter.

56. The method of any of paragraphs 46-55, wherein the heat is dry heat.

57. The method of paragraph 56, wherein the dry heat is at least 50° C.

58. The method of any of paragraphs 55-56, wherein the dry heat ranges from 65-95° C.

59. The method of any of paragraphs 46-58, wherein the composition is subjected to heat for at least 1 second.

60. The method of any of paragraphs 46-59, wherein the composition is subjected to heat for at least about 10 minutes.

61. The method of any of paragraphs 46-60, wherein the composition is subjected to dry heat at a first temperature, followed by subjecting the composition to dry heat at a second temperature.

62. The method of paragraph 61, wherein the first temperature is about 65° C. and the second temperature is about 85° C.

63. The method of any of paragraphs 61-62, wherein the composition is subjected to heat at the first temperature for at least about 1 to at least about 30 minutes and is subjected to heat at the second temperature for at least about 1 to at least about 30 minutes.

64. The method of any of paragraphs 61-63, wherein the composition is subjected to heat at the first temperature for about 30 minutes and is subjected to heat at the second temperature for about 10 minutes.

65. The method of any of paragraphs 61-63, wherein the composition is subjected to heat at the first temperature for about 30 minutes and is subjected to heat at the second temperature for about 30 minutes.

66. The method of any of paragraphs 46-55, wherein the heat is liquid heat.

67. The method of paragraph 66, wherein the liquid heat is at least about 50° C.

68. The method of paragraph 66, wherein the liquid heat is at least about 80° C.

69. The method of paragraph 66, wherein the liquid heat is at least about 82° C.

70. The method of any of paragraphs 66-69, wherein the composition is subjected to the heat for at least about one second.

71. The method of any of paragraphs 66-70, wherein the composition is subjected to the heat for at least about 5 minutes.

72. The method of any of paragraphs 66-70, wherein the composition is subjected to the heat for at least about 10 minutes.

73. The method of any of paragraphs 46-72, wherein the viability is enhanced at least about 2-fold compared with a composition that lacks the effective amount of amphipathic substance.

74. The method of any of paragraphs 46-72, wherein the viability is enhanced at least about 10-fold compared with a composition that lacks the effective amount of amphipathic substance.

75. The method of any of paragraphs 46-74, wherein the amphipathic substance is sunflower lecithin.

76. The method of any of paragraphs 46-75, wherein the ratio (w/w) of the amphipathic substance to the probiotic ranges from about 1:10 to about 25:1.

77. The method of any of paragraphs 46-76, wherein the ratio (w/w) of the amphipathic substance to the probiotic ranges from about 1:1 to about 10:1.

78. The method of any of paragraphs 46-77, wherein the ratio (w/w) of the amphipathic substance to the probiotic is about 5:1.

79. The method of any of paragraphs 46-77, wherein the ratio (w/w) of the amphipathic substance to the probiotic is about 10:1.

80. The method of any of paragraphs 46-79, wherein the composition is contacted with a food product and subjected to heat together with the food product.

81. The method of paragraph 46-79, wherein the subjecting the composition to heat step of part ii) comprises contacting the composition with a food product, wherein the food product had been previously subjected to heat prior to contacting the composition.

82. A method of treating a disease or condition characterized by inflammation in a subject in need thereof, comprising administering to the subject an effective amount of a *Pediococcus acidilactici* probiotic.

83. The method of paragraph 82, wherein the method comprises administering to the subject the composition of any of claims 1-34.

84. The method of paragraph 83, wherein the composition further comprises a food, nutraceutical or pharmaceutical product.

85. The method of any of paragraphs 82-84, wherein the disease or condition selected from the group consisting of malignancy (cancer), arthritis, cardiovascular disease, hepatitis, infection, wound healing, pancreatitis, gastroesophageal reflux disease, diabetes, inflammatory bowel disease, peptic ulcer disease, bronchitis, cholecystitis, appendicitis, bursitis, dermatitis, asthma, autoimmune disease, pelvic inflammatory disease, gout, trauma, foreign body infection, burns, dental work, tendonitis, rhinitis, mucositis, and exposure to toxins such as chemicals and alcohol.

86. The method of any of paragraphs 82-85, wherein the *Pediococcus acidilactici* probiotic is strain NRRL B-50517.

87. The method of any of paragraphs 82-86, wherein the subject is a human.

88. The method of any of paragraphs 82-87, wherein the subject is administered greater than $1.0 \times 10^9$ cfu of the probiotic.

89. The method of any of paragraphs 82-88, wherein the subject is administered greater than $4.0 \times 10^9$ cfu of the probiotic.

90. The method of any of paragraphs 82-89, wherein the subject is administered one or more additional therapeutic agents.

91. The method of any of paragraphs 82-89, wherein the subject is not administered another therapeutic agent.

92. The method of any of paragraphs 82-91, wherein the *Pediococcus acidilactici* probiotic increases the number of anti-inflammatory M2 macrophage cells in the subject.

93. The method of any of paragraphs 82-92, wherein the subject exhibits increased IL-10 production.

94. The method of any of paragraphs 82-93, wherein the subject exhibits decreased levels of IL-6 and/or IL-23.

95. The method of any of paragraphs 82-94, wherein the disease is cancer.

96. The method of paragraph 95, wherein the subject is administered one or more chemotherapeutic agents and/or radiotherapy in combination with the *Pediococcus acidilactici* probiotic.

97. The method of any of paragraphs 82-94, wherein the disease is pancreatitis.

98. A composition comprising an effective amount of *Pediococcus acidilactici* probiotic for use in the method of any of paragraphs 82-97.

99. The composition of paragraph 98, wherein the *Pediococcus acidilactici* probiotic is formulated as a tablet.

100. The composition of paragraph 98, wherein the *Pediococcus acidilactici* probiotic is formulated as a capsule.

101. The composition of any of paragraphs 98-100 comprising peach fruit powder as a flavorant.

102. The composition of any of paragraphs 98-101, wherein the *Pediococcus acidilactici* probiotic is strain NRRL B-50517.

The present invention is further illustrated by the following Examples. These Examples are provided to aid in the understanding of the invention and are not to be construed as a limitation thereof.

EXAMPLES

Example 1—*P. acidilactici* Administration Stimulates Innate Immune Responses in Animals This example describes the effect of administering *P. acidilactici* on innate immune responses in rats.

TABLE 1

Stimulation of macrophage activities on rats fed with *Pediococcus*-based probiotics

| | MAC* |
|---|---|
| Control | 4.0 ± 0.3 |
| Low | 4.0 ± 0.5 |
| Medium | 6.0 ± 1.6 |
| High | 7.2 ± 1.5 |

*Sprague Dawley rats (9 weeks) were fed Harlan #7012 rat chow ad libitum. The probiotic was *Pediococcus*-based probiotics (Imagilin, Frederick, MD). There were four groups (n = 10): control group (no probiotic); low dose ($1 \times 10^9$ cfu); mid group dose ($2 \times 10^9$); and high dose ($10 \times 10^9$). Animals were given 2 grams of food mixed with probiotic at 11 a.m. Then from 8 pm to 11 am, chow supplied ad libitum. Water was ad libitum 24 h. Tail blood samples were analyzed for complete blood counts.

When the rats were administered $2.0 \times 10^9$ to $10 \times 10^9$ cfu *Pediococcus*-based probiotics per day for 15 days, the amounts of macrophages increased 150% to 180% comparing to those from rats without probiotics. The increase of macrophages indicates that *Pediococcus*-based probiotics can stimulate rat innate immune responses. Interestingly, when rats were fed with low amounts ($1.0 \times 10^9$) of *Pediococcus*-based probiotics, the number of macrophages were similar to the amounts of macrophages as those from the control. This indicates that adequate amounts of *Pediococcus*-based probiotics are required to stimulate innate immune responses, such as increasing the amounts of macrophage cells.

Example 2—*P. acidilactici* Administration Stimulates Cytokine Production in Human Subjects This example describes the effect of administering *P. acidilactici* on cytokine production in human subjects.

For innate immune responses, macrophages are broadly divisible into two groups: pro-inflammatory M1 macrophages and anti-inflammatory M2 macrophages. The M2 macrophages also refers to macrophages that function in constructive processes like wound healing and tissue repair, and those that turn off damaging immune system activation by producing anti-inflammatory cytokines like interleukin-10 (IL-10).

TABLE 2

Increase of interleukin-10 (IL-10) on *Pediococcus* probiotics treated human volunteer subjects.

| | Detection of IL-6 | | | Detection of IL-10 | | |
|---|---|---|---|---|---|---|
| Participant ID | Before treated *Pediococcus* probiotics | After treated *Pediococcus* probiotics | % of IL-6 after treated *Pediococcus* probiotics | Before treated *Pediococcus* probiotics | After treated *Pediococcus* probiotics for 45 days | % of IL-10 after treated *Pediococcus* probiotics |
| AB01 | 0.50 | 0.29 | 58% | 1.99 | 3.99 | 200% |
| AB02 | 1.77 | 0.93 | 53% | 4.44 | 8.16 | 183% |
| AB03 | 1.94 | 1.72 | 89% | 5.66 | 8.95 | 158% |
| AB04 | 0.72 | 0.93 | 129% | 4.44 | 8.79 | 198% |
| AB05 | 0.12 | 0.19 | 158% | 0.77 | 3.25 | 422% |
| | | | Average 97.4% | | | Average 232% |

*: Serum samples were collected from five volunteers before administration of *Pediococcus acidilactici* NRRL B-50517 probiotics, and after administration of 4 billion cfu of *Pediococcus* probiotics per day for 45 days. Serum samples were analyzed using Luminex-based multiplex assays (EMD Millipore; Milliplex) designed to measure biomarkers associated with pro-inflammatory IL-6 and anti-inflammatory IL-10.

All five volunteers exhibited significantly increased anti-inflammatory IL-10 activity (from 158% to a 422% increase) after administration of *Pediococcus* probiotics for 45 days. On the contrary, the effect on pro-inflammatory IL-6 showed inconsistent results, which exhibited decreased activity in three volunteers and increased activity in two volunteers. These results demonstrate that administration of *Pediococcus* probiotics in human subjects may enhance more than two fold the anti-inflammatory IL-10 activity. These results, together with the results showing increases of macrophages in *Pediococcus*-based probiotics treated rats indicate that *Pediococcus*-based probiotics can enhance innate immunity of humans and animals. The innate immune responses of humans and animals treated with *Pediococcus* exhibit increases of M2 macrophage and anti-inflammatory IL-10.

Example 3—Effects of *P. acidilactici* NRRL B-50517 Supplementation for Use in Weight Management: A Controlled, Randomized, Double-Blind Trial This weight management study assessed the effect of a 12 week supplementation of *Pediococcus acidilactici* NRRL B-50517 probiotic strain on 30 adult participants in a controlled, randomized, double blind trial. Percent body fat was measured at the beginning and end of the trial with bioelectric impedance analysis (BIA). Levels of proinflammatory biomarkers interleukin-6 (IL-6) and interleukin-23 (IL-23) were determined using blood samples collected before the trial began and after it concluded. Appetite, energy level, bowel movement, stool quality, bloating, and gas, were monitored throughout the study using weekly questionnaires. The specific weight loss and anti-inflammatory effect of *P. acidilactici* is described here for the first time. Daily supplementation with 4 billion CFU *P. acidilactici* resulted in on average, the probiotic group lost 0.86±0.42% percent body fat whereas the control group gained 0.28%±0.19, p=0.0264. Pro-inflammatory IL-6 ratios differed by 0.61±0.22 and 3.06±0.87 in probiotic and control groups, respectively (p=0.0295); pro-inflammatory IL-23 ratio was 0.65±0.14 in the probiotic and 1.71±0.38 in the control groups, p=0.0068.

Methods and Materials

Participants in the study were selected on a volunteer basis; distribution of age, sex, and BMI was equal across treatment groups. Volunteers were not instructed to alter their regular dietary patterns or exercise routines during the study. The probiotic was tested in a group of subjects divided as such: 20% normal weight status (18.5-24.99), 47% overweight (25-29.99), and 33% obese (>30).

Prior to the beginning of the supplementation period, participants underwent an extensive physical exam including a bioelectric impedance analysis to determine body fat percentage and blood work to quantify IL-6 and IL-23 levels. The same exam procedure was repeated at the conclusion of the study. Over the course of 12 weeks, 30 participants were administered either 2 gelatin capsules containing a compound of *P. acidilactici* NRRL B-50517 fermentative cultures with peach fruit powders once daily, amounting to a dose of 4 billion CFU *Pediococcus* probiotics/day, or a placebo treatment of 2 capsules containing only peach powder. The safety of the probiotic was analyzed in terms of impact on appetite, energy level, bowel movement, stool quality, bloating, and gas. As part of a weekly questionnaire, participants were asked to score their experience of these symptoms on an arbitrary scale from 1 to 5, 1 being the least severe and 5 being the most severe.

Results

Figure 2:
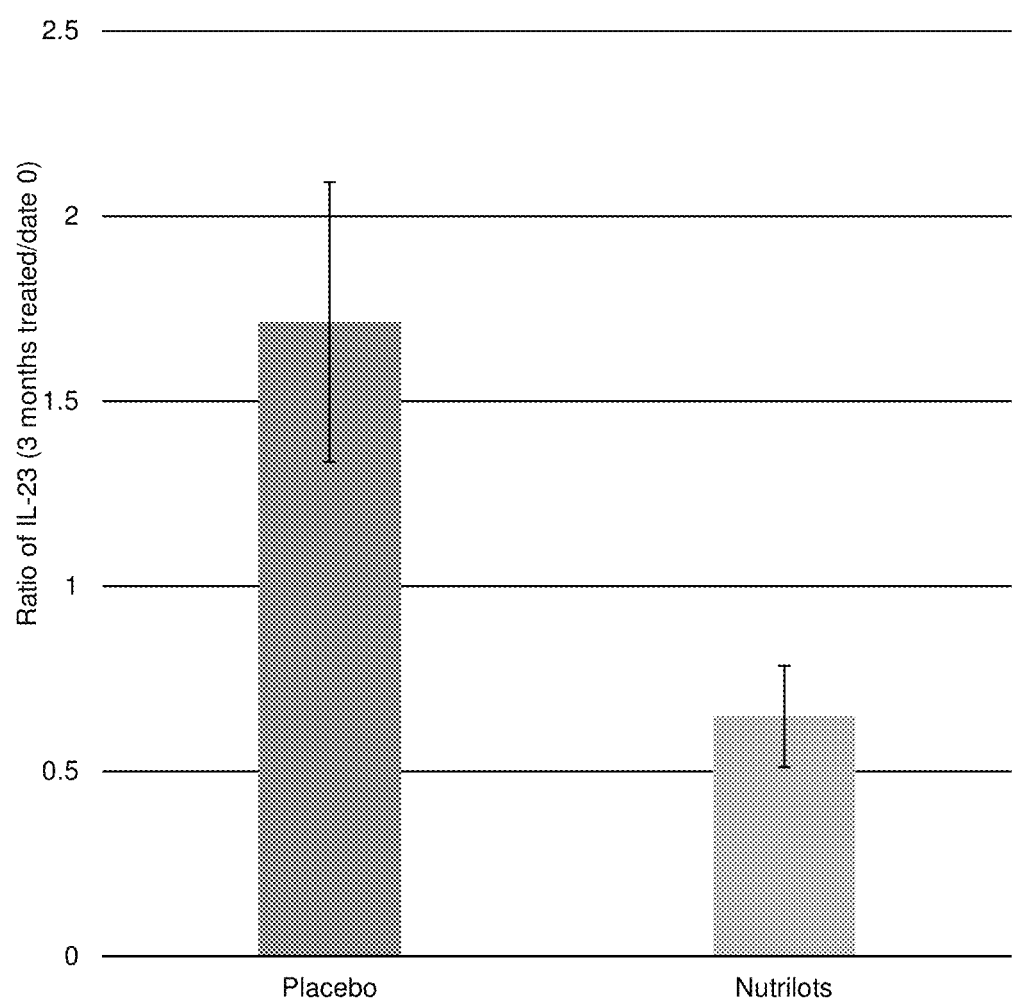
FIG. 2. Effect of *P. acidilactici* 5051 probiotic on IL-23 activity.
Figure 3:
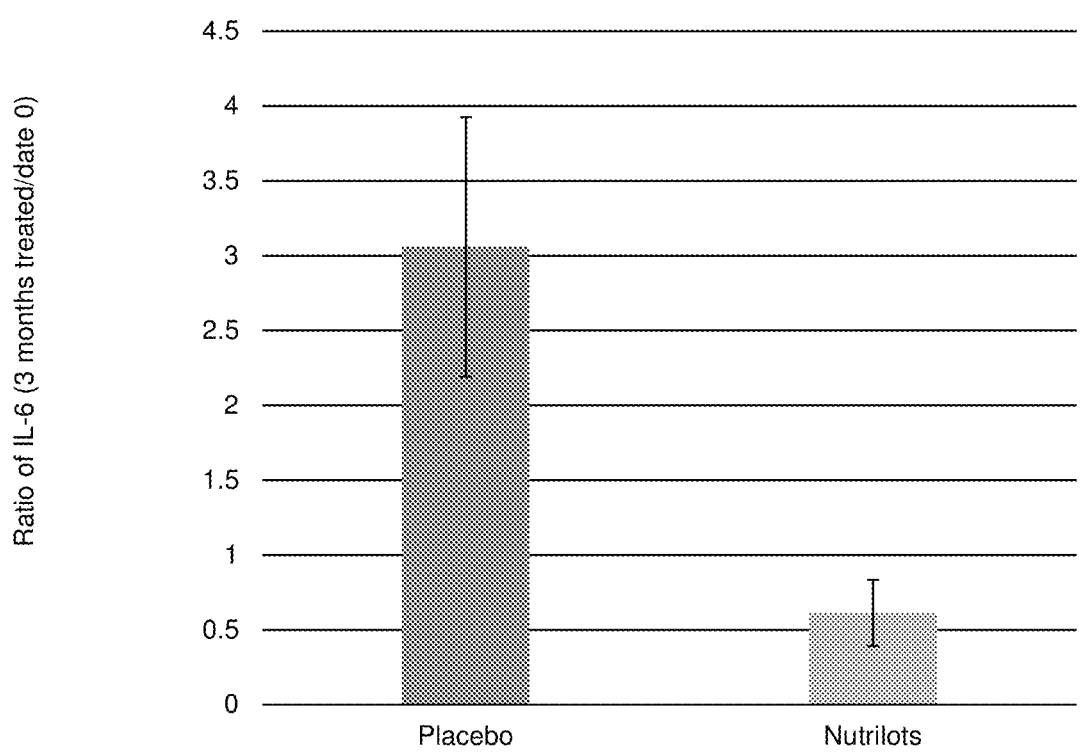
FIG. 3. Effect of *P. acidilactici* 5051 probiotic on IL-6 activity.

The present results show for the first time that supplementation of the probiotic *Pediococcus acidilactici* NRRL B-50517 to the diet of overweight and obese individuals alters bodily fat storage and influences concentration of inflammatory biomarkers linked to the pathology of obesity. The clear difference between % body fat, IL-6 and IL-23 levels observed between placebo and 5051-treated groups at the conclusion of the study demonstrate the effect of the probiotic to support weight loss even without traditional dietary modification or exercise. Results are shown in FIGS. 1-3. Error bars for all three graphs reflect that the respective values of percent body fat, IL-6, and IL-23 for the placebo and probiotic treated groups are not within one standard deviation of one another and thus signal a significant difference between the two.

Shown in FIG. 1 is the effect of *P. acidilactici* 5051 probiotic on body fat %. Participants were administered either 2 gelatin capsules containing a compound of *P. acidilactici* NRRL B-50517 fermentative cultures with peach fruit powders once daily, amounting to a dose of 4 billion CFU *Pediococcus* probiotics/day, or 2 capsules containing only peach powder. % body fat was determined by bioelectric impedance analysis (BIA) test. Values are based on double blind field evaluations of *Pediococcus* probiotics on total 30 volunteers for 3 months treatment. P=0.0264, t=2.4073, placebo mean=0.280±0.190 (SEM); NutriLots™ mean=−0.864±0.418 (SEM). The significantly higher difference in percent body fat observed in the probiotic-treated group (NutriLots) as compared to the placebo group after 3 months of treatment supports that *P. acidilactici* NRRL B-50517 supplementation can result in accelerated weight loss with no changes to diet or exercise patterns. Impact of *Pediococcus*-probiotic supplementation on Inflammatory Biomarkers IL-6 and IL-23.

Shown in FIG. 2 is the effect of *P. acidilactici* 5051 probiotic on IL-23. Blood samples were collected from each participant either with placebo or with probiotics before the study began and after the treatment period concluded to determine changes in IL-6 and IL-23 presence. Marked decreases in both IL-6 and IL-23 were observed in the *Pediococcus*-probiotic treated group. Values are based on double blind field evaluations of *Pediococcus* probiotics on total 30 volunteers for 3 months treatment. P=0.0295, t=2.4239, placebo mean=3.058±0.867 (SEM); NutriLots™ mean=−0.612±0.221 (SEM). The lower ratio of IL-23 in the probiotic-treated group (NutriLots) suggests that 5051 is capable of reducing obesity-related inflammation.

Shown in FIG. 3 is the effect of *P. acidilactici* 5051 Probiotic on IL-6. Values are based on double blind field evaluations of *Pediococcus* probiotics on total 30 volunteers for 3 months treatment. P=0.0068, t=3.0194, placebo mean=1.714±0.377 (SEM); NutriLots™ mean=−0.648±0.137 (SEM). The decreased ratio of IL-6 in the probiotic treated group (NutriLots) indicates that 5051 is capable of reducing obesity-related inflammation.

Discussion

In the present study, the 12-week *P. acidilactici* NRRL B-50517 probiotic treatment produced significant decreases in body fat percent, interleukins 6 and 23 when administered to participants of varying BMI (FIGS. 1, 2, and 3). Consistent results across the board indicate that the means of *P. acidilactici* action is not limited exclusively to individuals of obese weight status, but for those who are of lower BMI as well. A majority of previous studies have demonstrated the efficacy of LAB probiotic treatment on solely obese subjects. Where other probiotic strains were ineffective in reducing in the presence of obesity-related inflammation, 5051 decreased levels of both interleukins 6 and 23 as compared to the placebo group.

Safety of the probiotic was confirmed in a separately published study conducted alongside the present research. No significant difference in participant scores of appetite, bowel movement, bloating, stool quality, energy level, or gas was observed between the beginning and conclusion of the trial period in either the placebo or probiotic-treated group.

These findings have tremendous implications for future treatment and prevention of metabolic disease. As a large percentage of the cases of chronic conditions such as cardiovascular disease (CVD) and type 2 diabetes are developed in tandem with obesity, improving the management of this one disease has the potential to considerably reduce the incidence of several other prominent threats to public health.

While previously thought to only act as storage vessels for excess calories in the form of triglycerides, adipocytes have been discovered to play a complex role in metabolism, immunity, and cancer (Calabro P, Yeh E T H. 2007. Obesity, Inflammation, and Vascular Disease: the role of the adipose tissue as an endocrine organ. Subcellular Biochemistry. 42:63-91). White adipose cells secrete proteins including cytokines and hormone-like factors such as adiponectin, leptin, and resistin; this phenomenon is of particular interest because of the involvement of these molecules in vascular and metabolic complications (Calabro P, Yeh E T H. 2007. Obesity, Inflammation, and Vascular Disease: the role of the adipose tissue as an endocrine organ. Subcellular Biochemistry. 42:63-91). In a majority of obese patients, low grade inflammation of white adipose tissue (WAT) resulting from chronic activation of innate immunity poses an increased possibility of insulin resistance, impaired glucose tolerance, and eventual development of diabetic tendencies (Bastard J P, Maachi M, Lagathu C, Kim M J, Caron M, Vidal H, Capeau J, Feve B. 2006. Recent advances in the relationship between obesity, inflammation, and insulin resistance. Eur. Cyt. Net. 17(1): 4-12). Macrophage infiltration of obese WAT acts as a source of pro-inflammatory cytokines, further contributing to the pathogenesis of insulin resistance. Meanwhile, circulating levels of adiponectin, an insulin-sensing effector highly expressed in WAT, are lower in obese than normal weight subjects. The WAT in these individuals overproduces and secretes increased levels of numerous inflammatory molecules including IL-6, another modulator of insulin sensitivity. Thus, the pro-inflammatory pathogenesis of obesity and systemic development of insulin resistance are closely entwined, linked by the modulation of WAT.

Regulation of calorie extraction from dietary substances could be considered a possible mechanism of probiotic action for the results shown here. The composition of human gut microbiota has been consistently implicated as a determinant of body weight as a result of its critical role in nutrient acquisition and energy harvest and regulation (Tennyson C A, Friedman G. 2008. Microecology, obesity, and probiotics. Curr. Opin. Endocr. Diab. Obes. 15(5):422-7; DiBaise J K, Zhang H, Crowell M D, Krajmalnik-Brown R, Decker G A, Rittmann B E. 2008. Gut microbiota and its possible relationship with obesity. Mayo Clinic Proceedings. 83(4):460-69.). There is reason to believe that targeted microbial community moderation through the introduction of a probiotic could then have potential as a novel therapeutic agent in the treatment of metabolic disease. Conscious editing of the microbiome may be the key to reconcile the imbalance between energy intake and expenditure attributed to the obese state.

Unchanged reported scores for appetite in both the placebo and probiotic-treated groups indicate no potential alterations in dietary patterns or influence on satiety hormone leptin.

In decreasing body fat percent while simultaneously lowering serum IL-6 concentration, it can be presumed that *P. acidilactici* 5051 may increase insulin sensitivity and decrease overall systemic inflammation, therefore contributing to lowered risk of type 2 diabetes. As IL-6 is also linked to vascular damage in obese individuals, a lowered serum level of the cytokine would be likely to reduce risk of CVD (Calabro P, Yeh E T H. 2007. Obesity, Inflammation, and Vascular Disease: the role of the adipose tissue as an endocrine organ. Subcellular Biochemistry. 42:63-91). Inflammatory activity in obese individuals, increasing in accordance with WAT macrophage infiltration, can be assumed to decrease upon a loss in body fat.

The results shown here mirror those observed in an analysis of post-surgical results in morbidly obese individuals. Following bariatric surgery, patients have shown clinically relevant decreases in IL-6, triglycerides, cholesterol, LDL, glucose, and insulin correlated to BMI, validating the existence of a relationship between weight and the inflammatory profile, and further elucidating that between BMI and biochemical parameters of chronic metabolic and vascular conditions (Illan-Gomez F, Gonzalvez-Ortega M, Orea-Soler I, Alcaraz-Tafalla M S, Aragon-Alonso A, Pascual-Diaz M, Perez-Paredes M, Lozano-Almela M L. 2012. Obesity and inflammation: change in C-reactive protein, tumor necrosis factor-alpha and interleukin-6 after bariatric surgery. Obes. Surg. 22:950-55).

The marked decrease in IL-23 concentration observed in the probiotic-treated group is also a powerful signifier of lowered disease risk. IL-23/IL-17 is strongly associated with activation of signal pathways leading to tumor formation and the pathway for carcinogenesis. Because stimulation of the IL-23/IL-17 axis has been observed in obese women independent of increases in abdominal fat, insulin resistance, leptin, or MIF levels, it is reasonable to assume that dietary and behavioral patterns associated with the development of obesity, and not the obese state itself, may be responsible (Sumarac-Dumanovic M, Stevanovic D, Ljubic A, Jorga J, Simic M, Stamenkovic-Pejkovic D, Starcevic V, Trajkovic V, Micic D. 2009. Increased activity of interleukin-23/interleukin-17 proinflammatory axis in obese women. Int. J. Obes. 33:151-56).

Conclusions

In summary, the probiotic *P. acidilactici* NRRL B-50517 showed lowering effects on body fat percent, IL-6, and IL-23, suggesting its beneficial influence on weight management and metabolic disease. In light of the evidence set forth in this study, *Pediococcus acidilactici* NRRL B-50517 could prove to be effective in reduction of body fat and inflammation among those individuals seeking to lose weight.

Figure 4:
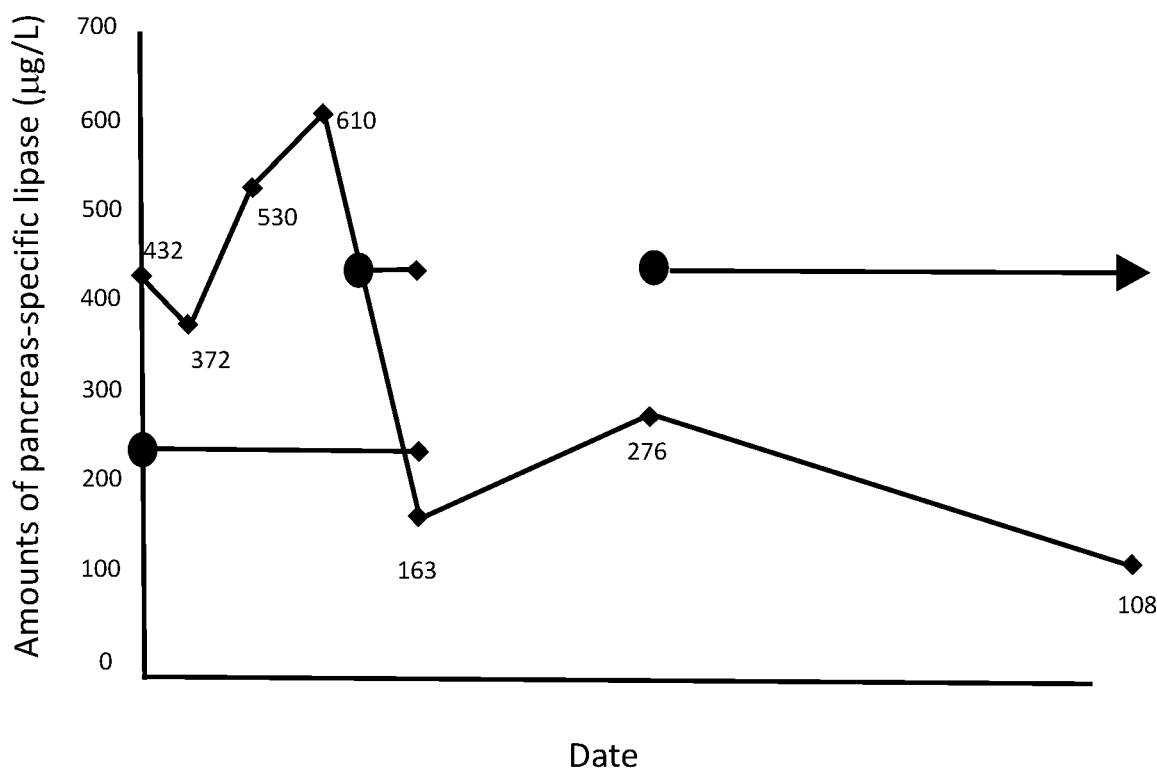
FIG. 4. Effects of *Pediococcus*-based probiotics on a dog with pancreatitis. A 14 years old, female, spayed toy poodle with pancreatitis was treated 100 mg KAMOSTAAL100 twice a day at a point in time (red dot), and the treatment was stopped about 2½ months later (red square). *Pediococcus*-based probiotics were applied (green dot), and stopped at about a month later (green square). After the relapse, *Pediococcus*-based probiotics were applied again (green circle), and continued for a period of time (green arrow).
Figure 5:
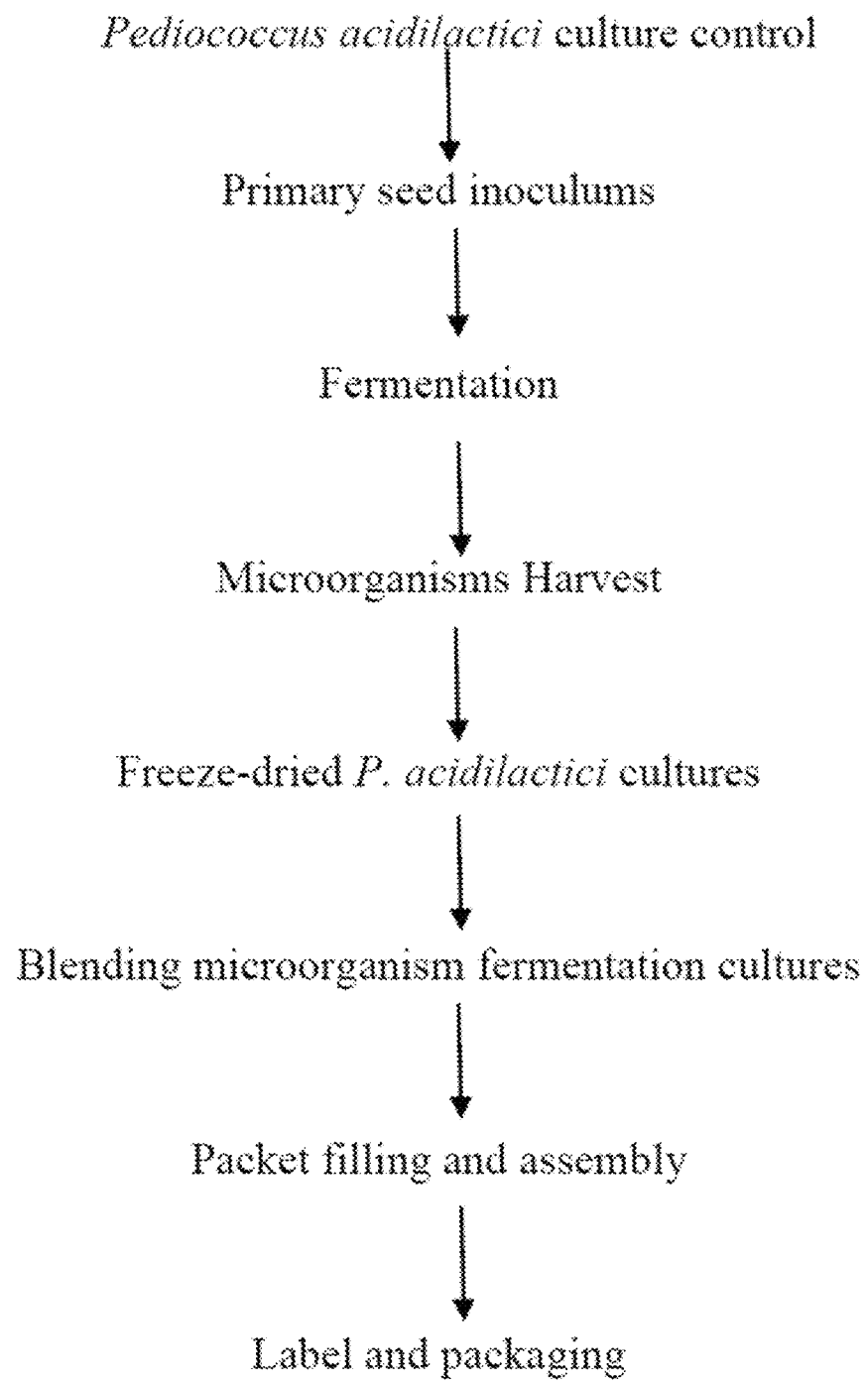
FIG. 5. *Pediococcus acdilactici* NRRL B-50517 manufacture process summary flow chart.
Figure 6:
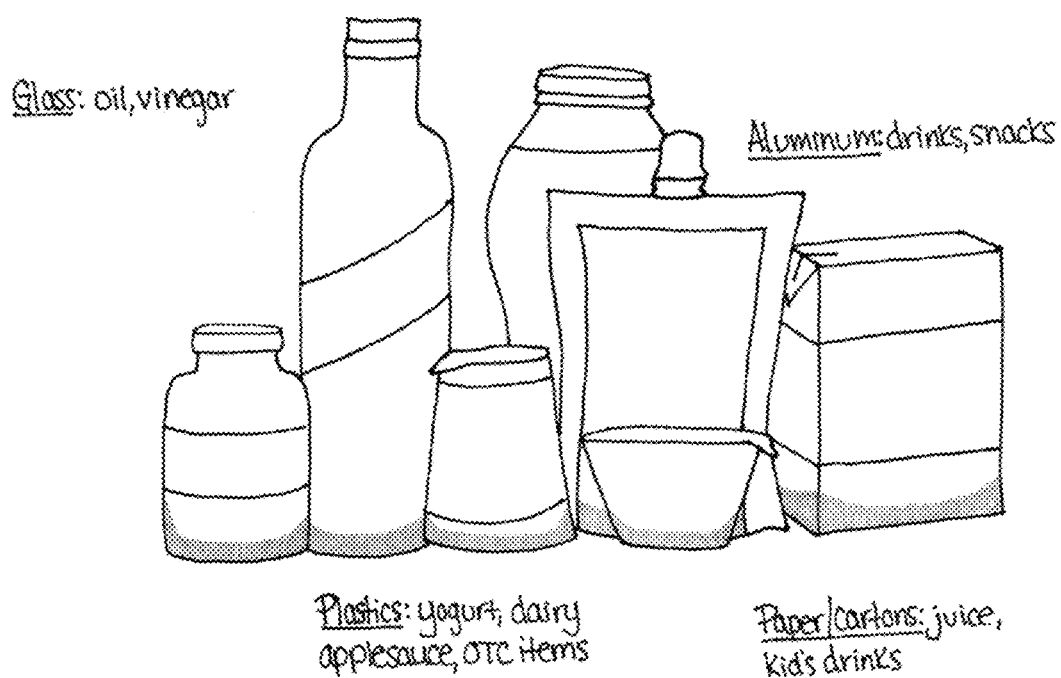
FIG. 6. Exemplary containers for food products comprising probiotic compositions.

Example 4—Effects of *Pediococcus* Based Probiotics on Dogs and Cats with Pancreatitis A 14 years old, female, spayed toy poodle with significant abdominal pain, vomiting and drop in appetite was diagnosed to possibly suffer from pancreatitis. The images of the ultrasound were shown to have high fats echo from the stomach to the duodenum, and the results of the serum analysis were shown to have spec cPL (Specific Canine Pancreatic Lipase) of 432 ug/L. Although the dog was switched to a low fat diet and treated 100 mg KAMOSTAAL100 twice a day immediately, the spec cPL remained high above 400 and reach 610 ug/L about 2.5 months thereafter with diarrhea and vomiting. At that point, the dog was treated twice a day of 200 mg *Pediococcus*-based probiotics together with current treatment of low fat diet and twice a day 100 mg KAMOSTAAL100. Interestingly, not only diarrhea and vomiting were stopped, the spec cPL was back to normal at 163 ug/L within about 6 weeks. Therefore the treatment of both *Pediococcus*-based probiotics and KAMOSTAAL100 was stopped. However, about three months later, the dog had a relapse with the spec cPL increased to 276 ug/L. At this time, the dog was treated was *Pediococcus*-based probiotics 200 mg twice a day only. The treatment was continued for about 7 months with good control of diarrhea, vomiting, and loss of appetite, and the spec cPL was shown to be normal at 108 ug/L (FIG. 4).

The spec cPL (Specific Canine Pancreatic Lipase) and the spec fPL (Specific Feline Pancreatic Lipase) are the normal spec cPL of canine and are the well-established assays for pancreatitis in dogs and cats. In healthy dogs and cats, the spec cPL is <200 ug/L, and the spec fPL is 0.7-3.5 ug/L. Dogs and cats are regarded to have pancreatitis, when spec cPL is greater than 400 ug/L and the cat spec fPL is >5.4 ug/L. Based on this criteria, we applied *Pediococcus*-based probiotics on two dogs and one cat, of which both dogs had spec cPL>600 ug/L, and the cat had spec fPL 50 ug/L, suffering from pancreatitis. All of these dogs and cats, not only the vomiting and diarrhea were stopped but also the spec cPL and spec fPL were controlled and returned to normal. Moreover, two dogs with possible pancreatitis were also treated, since they had elevated spec cPL (303 ug/L and 205 ug/L).

Example 5—Effects of *Pediococcus* Based Probiotics on the Dogs with Cancers Under Chemotherapy Treatment Four dogs having various cancers and that were undergoing chemotherapy were treated with doses of *Pediococcus* probiotics. After a short period of treatment with the *Pediococcus* probiotics, the dogs experienced improved symptoms.

| Age | Body weight (kg) | Sex | Cancer | Drugs for chemotherapy | Side effects before treatment | Dose of *Pediococcus* | Days of treatment | Improvement |
|---|---|---|---|---|---|---|---|---|
| 16 | 6 | Spayed | Breast cancer-surgery 3rd time | panriifu (anti-breast cancer drug: Tamoxifen) | Diarrhea, lost appetite | 2 billion cfu/day | 3 days | After administered *Pediococcus* based probiotics with anti-cancer drug for 3 days, vomiting stopped, lost appetite recovered. |
| 5 | 16.2 | Castrated | lymphoma | Adriamycin | General clinical condition is good | 4 billion cfu/day | 7 days | Good |
| 12 | 15.7 | Castrated | anal cystoma | Carboplatin | Soft stool | 4 billion cfu/day | 3 days | Good |
| 10 | 35 | female | lymphoma | L-asparaginase (Leunase), Chlorambucil, Prednisolone, Ulcerlmin (Sucralfate hydrate) | vomiting, diarrhea | 8 billion cfu/day | 4 days | Good after 4 days of treatment, diarrhea recovered |

*: The chemotherapy treatment and *Pediococcus* based probiotics administration treatment were performed at Daktari Animal Hospital Central, Toni, and Yaizu.

Example 6—Manufacture of *Pediococcus acdilactici* NRRL B-50517

First the strain needed for the fermentation process is selected from the bacteria being cryoed at −70° C. freezer. Grow the culture in sterile media bottles. When grown, pull samples to verify cleanliness and basic phenotypical purity. If determined to be clean and the cells match initial gram stain smears, approval to make the media (fermentation broth) for the tanks is given. Prior to inoculation, the inoculum tank is CIP'd (Clean In Place) with caustic and acid solutions. We sanitize the tanks prior to filling them with the broth fermentation ingredients which are dumped, mixed, and sterilized. The tank media is sterilized at 220° F.-250° F. for thirty minutes to an hour and a half depending on the volume of the tank. We then bring down the temperature to 85-95° F. to seed the tank with the inoculum. When the inoculation tank is grown, we cool the tank to 55-65° F. When cool, a sample is taken for repeated purity checks. If approved for release then, we repeat the steps for tank preparation and inoculation. Production will inoculate the tanks with the grown and approved inoculum bottles. After all the desired tanks are grown, we repeat the purity checks prior to prepping the centrifuge and concentrating the cells into a condensed liquid. The condensed liquid culture is put into a sterile holding tank. We add sterile liquid cryoprotectant solution to the centrifuged culture.

It is homogenized in the holding tank by the agitator. When homogenous, the culture is pumped into a sterile kettle (which is a functional aliquot for the cryofreezing or pelletizing of the product) to be pelletized in a liquid nitrogen vat. When complete the frozen pellets are lyophilized or freeze dried. After drying, we mill the freeze dried pellets into a fine powder. We will take the ground culture and homogenize it to ensure uniformity prior to sampling the culture for the quality assurance tests by morphological, physiological, 16S rRNA DNA sequences, and high temperature stress assays. Product is removed from the blender that was used to homogenize the material and then bag and store it at cool area, room temperatures.

Example 7—Formulation and Testing of *Pediococcus acdilactici* NRRL B-50517 in Food As knowledge of the health benefits of probiotics spreads and the demand for probiotic-infused food products continues to rise, food corporations are faced with a new set of challenges as they begin to collaborate with biotechnology companies. First, they must select one or more probiotic strains from the plethora of available options. Ideally, the chosen bacteria would need to: 1. Survive any manufacturing stress such as high heat treatment, 2. Possess compatibility with the chemical and physical properties of the desired food matrix, 3. Maintain viability in the food for the duration of the product's shelf life once incorporated, and 4. Resist destruction by digestive mechanisms in order to confer its health benefits to the host. Many probiotic strains popular in commercial supplements (such as *Lactobacillus* and *Bifidobacterium*) do not effectively fulfill these requirements and are thus unsuitable for industrial food production. Lacking the critical high heat resistance necessary to survive in recently pasteurized food, the applications of the two lactic acid bacteria (LAB) are severely limited in this context. The instability of these strains at room temperature would present additional complications in transport and storage for both food retailers and potential consumers. As facultative anaerobes to obligate anaerobes, *Lactobacillus* and *Bifidobacterium* would be especially vulnerable to losses in viability upon any exposure to oxygen, further reducing their potential for incorporation to food products. A more versatile, reliable strain is required to formulate effective probiotic-infused food.

*Pediococcus acidilactici* NRRL B-50517 is a uniquely formulated powder composed of the strain of bacteria capable of withstanding great variation in temperature, osmotic pressure, and oxygen exposure. A durable microorganism originally isolated from plant material, the probiotic has proven ability to survive in a wide range of food products under varying environmental conditions and heat treatment procedures.

Survival of *P. acidilactici* NRRL B-50517 in sucrose solutions ranging in concentration from 10 to 50% is indicative of probiotic resistance to osmotic pressure (Table 3). Where weaker bacteria would likely lose viability in a solution with comparably high osmolality, *P. acidilactici* NRRL B-50517 retains remarkably steady cell counts even at the highest tested concentration. Comparable results were obtained in solutions of lactose within the same concentration range over the course of 9 days (Table 4). In solutions of sterile water, 0.1 to 20% NaCl, and combined solutions of NaCl and sucrose, *P. acidilactici* NRRL B-50517 maintained significant cell viability in all assayed samples for up to one week, showcasing probiotic ability to adapt to a myriad of chemical environments (Table 5).

TABLE 3

Survival of *P. acidilactici* NRRL B-50517 incubated in high concentratedsucrose solution stored at room temperature
Numbers of *P. acidilactici* NRRL B-50517 viable cells after different incubation time in sucrose solution at room temperature

| % Sucrose solution | Control | 1 day | 3 days |
|---|---|---|---|
| 10% | 3.00E+08 | 5.20E+09 | N/A |
| 20% | 3.50E+08 | 3.00E+08 | 1.40E+08 |
| 30% | 3.30E+08 | 2.10E+08 | 1.50E+08 |
| 40% | 5.10E+08 | 3.70E+08 | 3.10E+08 |
| 50% | 6.50E+08 | 4.70E+08 | 3.30E+08 |

*: 0.2 g 1 Billion (1B) CFU/g *P. acidilactici* NRRL B-50517 was added to 20 mL of each sucrose solution and stored at room temperature. Viability tests were conducted by serially diluting sucrose + *P. acidilactici* NRRL B-50517 solution in 0.1% saline, plating onto MRS, and enumerating plates after overnight incubation.
**plates were contaminated on the third day, preventing continued testing for stability.

Conclusions: *P. acidilactici* NRRL B-50517 maintains viability in sucrose solutions ranging in concentration from 10-50%, indicating resistance of *P. acidilactici* NRRL B-50517 to high osmotic pressure environment

TABLE 4

Survival of *P. acidilactici* NRRL B-50517 incubated in high concentrated lactose solution stored at room temperature
Numbers of *P. acidilactici* NRRL B-50517 viable cells after different incubation time in lactose solution at room temperature

| % Lactose | Control | 1 day | 3 days | 7 days | 9 days |
|---|---|---|---|---|---|
| 10% | 1.20E+08 | 2.10E+08 | 1.90E+08 | 2.00E+08 | 8.00E+07 |
| 20% | 1.80E+08 | 1.40E+08 | 2.40E+08 | 2.10E+08 | 2.00E+08 |
| 30% | 2.30E+08 | 1.60E+08 | 4.30E+08 | 2.00E+08 | 1.60E+08 |
| 40% | 4.90E+08 | 3.70E+08 | 3.30E+08 | 3.67E+09 | 4.00E+08 |
| 50% | 1.80E+08 | 7.00E+07 | 1.00E+08 | 1.00E+09 | 1.50E+08 |

*: 0.2 g 1 B/g *P. acidilactici* NRRL B-50517 was added to 20 mL of each lactose solution and stored at room temperature. Viability tests were conducted by serially diluting sucrose + *P. acidilactici* NRRL B-50517 solution in 0.1% saline, plating onto MRS, and enumerating plates after overnight incubation.

Conclusions: Over a period of 9 days, *P. acidilactici* NRRL B-50517 retained highly stable viable cell counts in 10% to 50% lactose solutions.

TABLE 5

Survival of *P. acidilactici* NRRL B-50517 incubated in high salt solution stored at room temperature
Numbers of *P. acidilactici* NRRL B-50517 viable cells after different incubation time in salt solution at room temperature

| Solution | 5 min | 30 min | 120 min | 7 days | 14 days | 22 days | 35 days |
| --- | --- | --- | --- | --- | --- | --- | --- |
| Sterile H2O only | 4.13E+08 | 4.31E+08 | 4.03E+08 | 1.01E+08 | 4.90E+05 | 0.00E+00 | 0.00E+00 |
| 0.1% NaCl | 3.88E+08 | 3.82E+08 | 3.72E+08 | 1.82E+08 | 9.80E+07 | 1.60E+07 | 1.10E+05 |
| 1% NaCl | 4.38E+08 | 3.98E+08 | 3.51E+08 | 1.82E+08 | 2.90E+07 | 9.00E+04 | 5.00E+03 |
| 2.5% NaCl | 4.98E+08 | 3.87E+08 | 4.02E+08 | 2.21E+08 | 5.70E+07 | 1.00E+04 | 0.00E+00 |
| 5% NaCl | 4.85E+08 | 3.40E+08 | 3.87E+08 | 1.39E+08 | 1.25E+08 | 2.90E+07 | 1.01E+06 |
| 7.5% NaCl | 3.82E+08 | 3.72E+08 | 4.60E+08 | 6.70E+07 | 4.20E+07 | 2.90E+07 | 7.12E+06 |
| 10% NaCl | 4.32E+08 | 4.08E+08 | 4.96E+08 | 4.70E+07 | 7.00E+06 | 3.00E+06 | 2.60E+05 |
| 20% NaCl | 4.53E+08 | 3.62E+08 | 5.36E+08 | 1.03E+08 | 5.10E+07 | 3.20E+07 | 4.52E+06 |
| 25% Sucrose 10% NaCl | 3.92E+08 | 3.68E+08 | 4.80E+08 | 9.00E+07 | 5.60E+07 | 9.00E+06 | 1.56E+06 |

*: 0.2 g 1 B/g *P. acidilactici* NRRL B-50517 was added to 20 mL of different concentrations of NaCl or sucrose + NaCl solution and stored at room temperature. Viability tests were conducted by serially diluting NaCl + *P. acidilactici* NRRL B-50517 solution in 0.1% saline, plating onto MRS, and enumerating plates after overnight incubation.

When assayed extensively for viability, 5051® retained viable cell counts (CFU/g) for up to 113 days after incorporation to peanut butter when stored at room temperature, indicating high shelf stability (Table 6). The probiotic showed similarly successful results when heated to 85° C. in peanut butter with storage at room temperature thereafter. Stability was similarly constant when the probiotic was incorporated to 85° C.-heated pudding; cell counts remained within one log over a period of 29 days with refrigerator storage (Table 7).

TABLE 6

Integration of *Pediococcus acidilactici* NRRL B-50517 into commercial peanut butter
Numbers of viable cells after integrated *P. acidilactici* NRRL B-50517 into peanut butter stored at different temperature

| Days of storage | Room temperature | % Survival | 37° C. | % Survival |
| --- | --- | --- | --- | --- |
| Control | 3.15E+10 | 100.00 | 3.15E+10 | 100.00 |
| 0 | 2.78E+10 | 88.18 | n/a | n/a |
| 7 | 1.34E+10 | 42.68 | 1.63E+10 | 51.85 |
| 14 | 2.33E+10 | 74.07 | 1.78E+10 | 56.44 |
| 22 | 2.91E+10 | 92.24 | 1.49E+10 | 47.27 |
| 113 | 4.78E+09 | 15.17 | 2.00E+07 | 0.06 |

*: Samples of *P. acidilactici* NRRL B-50517 and peanut butter were prepared by mixing 6 g of 100 B/g *P. acidilactici* NRRL B-50517 powder with 20 g peanut butter, then stored at either room temperature (23° C.) or 37° C. Stability tests were conducted by adding 0.1 g of the mixture to 5 mL 0.1% saline, serially diluting the solution for plating onto MRS, and enumerating plates after overnight incubation at 45° C. Percent survival was calculated as a fraction of a *P. acidilactici* NRRL B-50517 + saline control (0.2 g 100 B/g *P. acidilactici* NRRL B-50517 added to 10 mL 0.1% saline at room temperature).

Conclusion: *P. acidilactici* NRRL B-50517 shows high cell counts (CFU/g) in peanut butter at room temperature over a period of 113 days, indicating that a product containing both ingredients would maintain high shelf stability. Even when stored at 37° C., the peanut butter and *P. acidilactici* NRRL B-50517 mixture displays similarly high viability over 22 days, dropping off between the 22 and 113 day viability tests.

TABLE 7

Survival of *P. acidilactici* NRRL B-50517 in peanut butter after high temperature (85° C.) treatment
Numbers of viable cells after heat treated integrated *P. acidilactici* NRRL B-50517 into peanut butter at 85° C. and stored at room temperature

| Peanut Butter | Day 1 | % Survival | Day 7 | % Survival | Day 14 | % Survival |
| --- | --- | --- | --- | --- | --- | --- |
| Control | 3.15E+10 | 100.00 | 3.15E+10 | 100.00 | 3.15E+10 | 100.00 |
| PB 1 | 7.98E+09 | 25.33 | 1.01E+09 | 3.22 | 2.22E+09 | 7.04 |
| PB 2 | 1.38E+10 | 43.83 | 3.17E+09 | 10.05 | 3.67E+09 | 11.66 |
| Hazelnut | 2.53E+08 | 0.80 | 7.66E+08 | 2.43 | 8.11E+08 | 2.57 |

*: Samples of *P. acidilactici* NRRL B-50517 and peanut butter were prepared by mixing 1.2 g of 100 B/g *P. acidilactici* NRRL B-50517 powder into 3.8 g peanut butter. Empty tubes were heated to 85° C. before 0.5 g peanut butter and *P. acidilactici* NRRL B-50517 mixture was added and left on the hot plate for 5 min. After a 10 min cooling period, 10 mL 0.1% saline was added to each tube. Viability tests were conducted by serially diluting into saline, plating onto MRS, and enumerating plates after overnight incubation at 45° C. Percent survival was calculated as a fraction of a *P. acidilactici* NRRL B-50517 + saline control (0.2 g 100 B/g *P. acidilactici* NRRL B-50517 added to 10 mL 0.1% saline at room temperature).

Conclusion: Over a period of two weeks after high heat treatment, *P. acidilactici* NRRL B-50517 maintained high viability in nut butters, supporting compatibility of the *P. acidilactici* NRRL B-50517 with commercially produced nut products.

PB1 ingredients: roasted peanuts, sugar, hydrogenated vegetable oil (cottonseed, soybean, and rapeseed oil) to prevent separation, salt.

Hazelnut Spread ingredients: sugar, vegetable oil (palm and rapeseed oil), hazelnuts, cocoa powder, skim milk, whey, lactose, sunflower lecithin (emulsifier), natural vanilla flavor.

Testing of *P. acidilactici* NRRL B-50517 in five types of high-heat treated oil (corn oil, EVOO, LTOO, peanut oil, and vegetable oil) produced results analogous to those observed in peanut butter. Two of the oils, EVOO and corn oil (Table 8), displayed impressive survival rates even after 30 minutes of continuous exposure to 85° C. (Table 9 and Table 10). The apparent durability of the probiotic in oil is particularly conducive to its use in traditional food preparation techniques which involve heat.

TABLE 8

Survival of P. acidilactici NRRL B-50517 in commercial oil after high temperature (85° C.) treatment
Numbers of viable cells after heat treated the integrated P. acidilactici NRRL B-50517 into different types of oils

| Oil Type | Room | % Survival | Up to 85° C. | % Survival | 5 min at 85° C. | % Survival |
| --- | --- | --- | --- | --- | --- | --- |
| Control | 2.75E+08 | 100.00 | 2.75E+08 | 100.00 | 2.75E+08 | 100.00 |
| Corn Oil | 6.75E+07 | 24.52 | 4.55E+07 | 16.53 | 6.00E+06 | 2.18 |
| EVOO | 9.70E+07 | 35.23 | 4.20E+07 | 15.25 | 1.10E+07 | 4.00 |
| LTOO | 5.90E+07 | 21.43 | 3.60E+07 | 13.08 | 5.30E+07 | 19.25 |
| Peanut Oil | 1.68E+08 | 61.02 | 2.30E+07 | 8.35 | 0.00E+00 | 0.00 |
| Vegetable Oil | 1.06E+08 | 38.50 | 4.70E+07 | 17.07 | 6.00E+06 | 2.18 |

*: 900 uL oil was heated to 85° C. on a hot plate before 0.1 g 1 B/g P. acidilactici NRRL B-50517 was added, then left for the specified period of time. Tubes were then removed and allowed to cool for a minimum of 10 min before serially diluting in 0.1% saline and plating on MRS. Plates were incubated overnight at 45° C. and enumerated the next day. Percent survival was calculated as a fraction of a saline + P. acidilactici NRRL B-50517 control (0.2 g 1 B/g P. acidilactici NRRL B-50517 added to 20 mL 0.1% saline at room temperature).

Conclusion: P. acidilactici NRRL B-50517 maintains high viable cell counts (CFU/g) in a variety of commercial oils at room temperature and after high temperature treatment.

TABLE 9

Effects on survival of P. acidilactici NRRL B-50517 in Olive oil after high temperature (85° C.) treatment at different time

| EVOO at different temperature | Numbers of viable cells after heat treated the integrated P. acidilactici NRRL B-50517 into olive oil | % Survival |
| --- | --- | --- |
| Room | 1.18E+08 | 100.00 |
| Up to 85° C. | 7.80E+07 | 66.10 |
| 85° C., 5 min | 1.90E+07 | 16.10 |
| 85° C., 15 min | 3.00E+05 | 0.25 |
| 85° C., 30 min | 2.00E+05 | 0.17 |

*: 900 uL oil was heated to 85 C. on a hot plate before 0.1 g P. acidilactici NRRL B-50517 was added, then left for the specified period of time. Tubes were removed from the heat source and allowed to cool for a minimum of 10 min before serially diluted and plated onto MRS. Plates were incubated overnight at 45° C. and enumerated the next day. Percent survival at each length of heat treatment was calculated as a fraction of survival in EVOO at room temperature.

Conclusion: P. acidilactici NRRL B-50517 survives high heat treatment in EVOO, producing high viable cell numbers even after 30 min at 85° C. The probiotic would likely be compatible for a variety of food preparation techniques, including those involving heating.

TABLE 10

Effects on survival of P. acidilactici NRRL B-50517 in corn oil after high temperature (85° C.) treatment at different time

| Corn Oil Temperature | Numbers of viable cells after heat treated the integrated P. acidilactici NRRL B-50517 into corn oil | % Survival |
| --- | --- | --- |
| Room | 6.50E+07 | 100.00 |
| Up to 85° C. | 6.30E+07 | 96.92 |
| 85° C., 5 min | 4.00E+06 | 6.15 |
| 85° C., 15 min | 5.30E+05 | 0.82 |
| 85° C., 30 min | 3.00E+04 | 0.05 |

*: 900 uL oil was heated to 85 C. on a hot plate before 0.1 g P. acidilactici NRRL B-50517 was added, then left for the specified period of time. Tubes were removed from the heat source and allowed to cool for a minimum of 10 min before serially diluted and plated onto MRS. Plates were incubated overnight at 37° C. and enumerated the next day. Percent survival at each length of heat treatment was calculated as a fraction of survival in corn oil at room temperature.

Conclusions: P. acidilactici NRRL B-50517 survives high heat treatment in corn oil, producing high viable cell numbers even after 30 min at 85° C. The probiotic would likely be compatible with a variety of food preparation techniques, including those involving heating.

P. acidilactici NRRL B-50517 can survive after 85° C. heat treated different food products dispenses into the different containers with P. acidilactici NRRL B-50517 simulated sterilization procedures used in the food industry (Table 11 and Table 12), and retain viability in products with diverse physiochemical properties for weeks or months. This provides a novel approach to introduce viable probiotics into foods.

TABLE 11

Survival of P. acidilactici NRRL B-50517 in pudding after high temperature (85° C.) treatment
Numbers of viable cells after heat treated the integrated P. acidilactici NRRL B-50517 into different types of pudding

| Days after 85° C., Treatment | Vanilla pudding | Chocolate pudding |
| --- | --- | --- |
| 1 | 3.55E+07 | 4.70E+07 |
| 2 | 6.90E+07 | 2.65E+07 |
| 3 | 6.05E+07 | 5.10E+07 |
| 6 | 3.60E+07 | 1.93E+07 |
| 14 | 3.55E+07 | 7.75E+06 |
| 29 | 6.10E+07 | 4.00E+06 |

*: A 100 mL cup of Shiny Spoon Pudding was emptied into two 50 mL tubes and heated to 85° C. for 20 min. The original container was cleaned with soap and water, dried, and filled with 2 g 10 B/g P. acidilactici NRRL B-50517. The heated pudding was then poured back into the original container, cooled for 20 min, then stored in the refrigerator overnight. The next day the pudding was mixed and assayed for viability by first diluting 2 g pudding in 5 mL saline, then serially diluting for plating onto MRS. Plates were incubated overnight and enumerated the following day.

Conclusion: After incorporation to either vanilla or chocolate pudding heated to 85° C. in conditions similar to pasteurization, P. acidilactici NRRL B-50517 maintains highly stable cell counts for approximately one month when stored at refrigerator temperature.

TABLE 12

Survival of P. acidilactici NRRL B-50517 in commercial food products after high temperature (85° C.) treatment

| Food Product | P. acidilactici NRRL B-50517 Survival After 85° C., Treatment CFU/g | % Survival |
| --- | --- | --- |
| Control | 2.75E+08 | 100 |
| Ketchup | 9.83E+07 | 35.68 |
| Fruit Cup | 8.19E+07 | 29.75 |
| EVOO | 7.55E+07 | 27.42 |
| Great Value Oil | 2.43E+07 | 8.81 |
| 2.5% Lactose | 2.33E+07 | 8.46 |
| Strawberries in Syrup | 1.40E+07 | 5.09 |
| Orange Juice | 1.04E+07 | 3.79 |

*: Samples were prepared as follows: 1. 10 mL ketchup was heated at 85° C. for 20 min, then mixed with 0.4 g of 1 B/g P. acidilactici NRRL B-50517 and 5 mL sterile water and allowed to cool for 20 min before testing for viability. 2. 100 g fruit cup mixture was heated at 85° C. for 45 min, then poured back into the original container over 1 g 1 B/g P. acidilactici NRRL B-50517 and tested for viability. 3. Tubes of 5 mL EVOO and Great Value oil were heated at 85 C. for 20 min, then added to 0.2 g 1 B/g P. acidilactici NRRL B-50517 and tested for viability. 4. A tube containing 5 mL 2.5% lactose was heated at 85° C. for 20 min, then added to a 15 mL tube containing 0.2 g 1 B/g P. acidilactici NRRL B-50517. The tube was allowed to cool for 20 minutes before testing for viability. 5. 283 g strawberry in syrup mixture was poured into a beaker, heated at 85° C. for 30 min, then poured back into original container on top of 2 g 1 B/g P. acidilactici NRRL B-50517. After cooling for 20 min, the mixture was tested for viability. 6. 5 mL orange juice was heated to 85° C. for 20 min, then added to 0.1 g 1 B/g P. acidilactici NRRL B-50517, cooled for 20 min and tested for viability.
**All viability testing was conducted by serially diluting P. acidilactici NRRL B-50517 + heat-treated food mixture in 0.1% saline, plating onto MRS, and enumerating plates after overnight incubation. Percent survival was calculated as a fraction of a saline + P. acidilactici NRRL B-50517 control (0.2 g 1 B/g P. acidilactici NRRL B-50517 added to 20 mL 0.1% saline at room temperature).

Conclusion: P. acidilactici NRRL B-50517 maintains viability in a variety of liquid and solid matrices after high heat treatment, indicating high compatibility for incorporation to many different foods after pasteurization or other similar high-heat sterilization procedures.

Example 8—Increase of Probiotic Viability Under Heat Treatment by Applying Amphipathic Products as the Carrier Amphipathic molecules are molecules having both polar and non-polar portions in their structure. The chemical compounds that feature these molecules are essential to a host of biological and industrial processes.

In this study, we apply amphipathic products such as lecithin, peanut butters, almond butters, soy butters and cookie butter as the alternative carriers of *Pediococcus acidilactici* NRRL B-50517 fermentative cultures. The excess amounts of amphipathic products can protect *P. acidilactici* NRRL B-50517 fermentative cultures from the harsh dry heat or wet heat treatment. After mixing dried powders of amphipathic products and bacterial freeze dried fermentative cultures with oil, the unique property of amphipathic products can form the lipid paste and function as carriers of the *P. acidilactici* fermentative cultures to withstand dry heat treatment or hot water treatment which is similar as pasteurization process for food treatment.

There are several approaches to include the probiotics to pasteurized food/feed products. The desirable approaches are including probiotics into the food/feed ingredients together, and then performing the pasteurization process, which can include hot water treatment. Alternatively, one can dispense the food/feed ingredients to the probiotics composition after pasteurization. This can be demonstrated by removing the hot water treated juices/liquids after the temperature of juices/liquids has reached the defined pasteurized temperature, and combining it with the mixtures of probiotics and amphiphilic products immediately. Therefore, the following experiments applied the hot water heat treatment to the mixtures of probiotics and amphipathic products together as the hot water/liquids reach desirable temperatures for immediately, 5 minutes and 10 minutes, then performed the assays to determine the numbers of live probiotics after these heat treatments. In these efforts, we can demonstrate that the amphiphilic products together with probiotics are able to go through the heat treatment such as a pasteurization process.

Lethicin is defined as phosphatidylcholine and stands for natural mixture of neutral and polar lipids from vegetable and animal sources. It has low solubility in water, but is an excellent emulsifier. In aqueous solution, its phospholipids can form either liposomes, bilayer sheets, micelles, or lamellar structures, depending on hydration and temperature. This results in a type of surfactant that usually is classified as amphipathic.

In this study, we apply amphipathic products such as lecithin, peanut butters, almond butters, soy butters and cookie butter as the alternative carriers of *Pediococcus acidilactici* NRRL B-50517 fermentative cultures. The excess amounts of amphipathic products are able to protect *P. acidilactici* NRRL B-50517 fermentative cultures from the harsh dry heat or wet heat treatment. After mixing dried powders of amphipathic products and bacterial freeze dried fermentative cultures with oil, the unique property of amphipathic products is able to form the lipid paste and carry the *P. acidilactici* fermentative cultures to make them more resistant to heat, such as hot water treatment.

TABLE 13

Dry heat treatment of the mixtures of lecithin with *P. acidilactici* fermentative cultures

| Probiotics | High temperature treatment | # of live *P. acidilactici* (cfu/g)* | % survival of *P. acidilactici* |
|---|---|---|---|
| *P. acidilactici* NRRL B-50517 | Control (Room temperature) | $1.68 \times 10^8$ | 100% |
| | 65° C. 30 min | $3.4 \times 10^7$ | 20.24% |
| | 65° C. 30 min + 85° C. 10 min | $4.0 \times 10^6$ | 2.38% |
| | 65° C. 30 min + 85° C. 30 min | $7.6 \times 10^5$ | 0.45% |
| *P. acidilactici* NRRL B-50517 + lecithin | Control (Room temperature) | $1.23 \times 10^8$ | 100% |
| | 65° C. 30 min | $1.00 \times 10^8$ | 81.63% |
| | 65° C. 30 min + 85° C. 10 min | $1.45 \times 10^7$ | 11.84% |
| | 65° C. 30 min + 85° C. 30 min | $6.00 \times 10^6$ | 4.90% |

*0.2 g of *P. acidilactici* NRRL B-50517 freeze dried fermentative cultures with maltodextrin as the carriers (1 billion cfu/g) were used for these tests. All heated samples. Temperature was verified with a digital probe. The samples were preheated at 65° C. for 30 mins then added to 85° C. dry heat over for the appropriate amount of time. The powder was removed from the heat and left at room temperature to cool for 10 mins. The dry powder was added to 5 ml saline, mixed and set in the saline for 5 mins and then plated onto MRS plates overnight at 37° C. incubator and scored for viability. 0.2 g (0.5 billion cfu/g) powders of the 1.75 g Sunflower Lecithin and 1.75 g *P. acidilactici* NRRL B-50517 (1 Billion cfu/g) were transferred onto weight paper. The samples were heated at 65° C. for 30 mins, then cooled for 10 mins. Transferred the other 65° C. treated samples to the 85° C. for 10 mins and 30 mins, then let it cool for 10 mins. Temperature was verified with a digital probe. Dissolve in 5 mls of saline, then performed to desirable dilution, and plate 100 ul onto MRS agar plates and incubated at 37° C. overnight for viability count.

Results:

Applied lecithin as the carriers of *P. acidilactici* freeze dried fermentative cultures improved the survival of bacteria under different heat treatment from 5 to 10-fold compared with those heat treated *P. acidilactici* freeze dried fermentative cultures only.

TABLE 14

Wet heat treatment of the mixtures of lecithin with *P. acidilactici* fermentative cultures

| Heat Treatment Temperature | Incubation time | # of live *P. acidilactici* (cfu/g)* | % of survival |
|---|---|---|---|
| 80° C. | Immediately | $1.18 \times 10^8$ | 37.11% |
| | 5 minutes | $4.16 \times 10^7$ | 13.08% |
| | 10 minutes | $2.38 \times 10^6$ | 0.75% |
| 82° C. | Immediately | $2.58 \times 10^7$ | 8.11% |
| | 5 minutes | $1.28 \times 10^6$ | 0.40% |
| | 10 minutes | $3.00 \times 10^4$ | 0.01% |
| Room temperature | — | $3.18 \times 10^8$ | 100% |

*transferred 0.5 g sample [1.4 g *P. acidilactici* NRRL B-50517 freeze dried fermentative cultures (10 Billion cfu/g) + 8 g sunflower lecithin + 9 mL olive oil] to an Eppendorf tube with 1 ml distilled water and incubated at 80° C. or 82° C. water bath for different time-immediately after distilled water in the tube reached 80° C. or 82° C., continued to incubate at 80° C. or 82° C. for 5 minutes or 10 minutes, removed the tubes from water bath, then let it cool for 10 mins, performed to desirable dilution, and plate 100 ul onto MRS agar plates and incubated at 37° C. overnight for viability count. Temperature was verified with a digital probe.

Results:

The mixtures of *P. acidilactici* NRRL B-50517 and sunflower lecithin were re-suspended with olive oil as the pastes and were submerged in the water for heat treatment at 80° C. and 82° C. When the heated bacterial pastes were removed from the hot water temperature when it reached 80° C., the treated bacterial paste products were transferred to room temperature for cooling down process, more than 37% of viable bacteria was detected. Similarly heat treatment up to 82° C., about 8.0% viable cells were detected. These heat treatment process is applying probiotics after product through pasteurization process, and dispenses these hot products directly to the *P. acidilactici* fermentative cultures with amphiphilic products in the containers.

TABLE 15

Stability of mixtures of lecithin and *P. acidilactici* stored at room temperature and 37° C. incubators

| Days of storage | Room temperature* ($\times 10^8$ cfu/g) | 37° C.* ($\times 10^8$ cfu/g) |
|---|---|---|
| Day 1 | 5.96 | 9.93 |
| Day 2 | 5.59 | 8.33 |
| Day 7 | 4.93 | 2.24 |
| Day 14 | 5.06 | 4.78 |
| Day 28 | 8.41 | 5.74 |
| Day 44 | 12.80 | 13.0 |
| Day 60 | 5.03 | 3.63 |
| Day 91 | 5.90 | 2.48 |

*Each sample had 1.4 g 10 B/g 5051 mixed into 7 g sunflower lecithin powder (1.67 B cfu/g). Made 4 samples: A and B at room temp and a different A and B placed in 37° C. incubation. Added in desiccant packets. Tested with dilutions using 0.2 g powder in 5 mL saline, mixed homogenously by vortex for 30 seconds, and performed series of dilution with saline, and plated 100 ul of desirable dilution onto MRS plates overnight at 37° C. and counted the individual colonies Results:

The mixtures of lecithin and *P. acidilactici* freeze dried fermentative cultures were stable either stored at room temperature or 37° C. for more than 90 days. The viability of *P. acidilactici* remains similar amounts of viable cells through the storage at both room temperature and 37° C.

TABLE 16

Effects of Lecithin on improvement of *Pediococcus acidilactici* NRRL B-50517 survival in soy sauce after 80° C. heat treatment

| Incubation time at 80° C. water bath | # of live *P. acidilactici* (cfu/g)* | % of survival |
|---|---|---|
| Immediately | $2.00 \times 10^8$ | 75.19% |
| 5 minutes | $2.06 \times 10^7$ | 7.74% |
| 10 minutes | $3.32 \times 10^6$ | 1.25% |
| Control (no heat treatment) | $2.66 \times 10^8$ | 100% |
| Control (no heat treatment) | $3.06 \times 10^8$ | 100% |

*Transferred 0.5 gram of the pastes including 0.7 gram *P. acidilactici* NRRL B-50517, 10 billion cfu/g, 3.5 gram sunflower lecithin, and 4.5 ml olive oil into an Eppendorf tube with 1 ml soy sauce, and incubated at 80° C. water bath. When the temperature of soy sauce reach 80° C., 1) immediately; 2) incubated at 80° C. for 5 minutes, 30 incubated at 80° C. for 10 minutes, then removed the tube from water bath, mixed homogenously by vortex for 30 seconds, and performed series of dilution with saline, and plated 100 ul of desirable dilution onto MRS plates overnight at 37° C. and counted the individual colonies. Temperature was verified with a digital probe.

TABLE 17

Effects of Lecithin on improvement of *Pediococcus acidilactici* B-50517 survival in different juice after 80° C. heat treatment

| Juice | Incubation time 80° C. water bath | # of live *P. acidilactici* NRRL B-50517 (cfu/g)* | % of survival |
|---|---|---|---|
| V8 juice | Immediately | $6.40 \times 10^7$ | 42.95% |
| | 5 minutes | $9.28 \times 10^6$ | 6.23% |
| | 10 minutes | $1.07 \times 10^7$ | 7.18% |
| | Control (no heat treatment) | $1.49 \times 10^8$ | 100% |
| Lemonade | Immediately | $1.92 \times 10^8$ | 42.11% |
| | 5 minutes | $1.04 \times 10^7$ | 2.28% |
| | 10 minutes | $4.64 \times 10^6$ | 1.02% |
| | Control (no heat treatment) | $4.56 \times 10^8$ | 100% |
| Cranberry juice | Immediately | $6.00 \times 10^7$ | 37.50% |
| | 5 minutes | $1.10 \times 10^7$ | 6.88% |
| | 10 minutes | $5.84 \times 10^5$ | 0.37% |
| | Control (no heat treatment) | $1.60 \times 10^8$ | 100% |
| Pear juice | Immediately | $7.92 \times 10^7$ | 13.38% |
| | 5 minutes | $5.60 \times 10^6$ | 0.95% |
| | 10 minutes | $6.56 \times 10^6$ | 1.11% |
| | Control (no heat treatment) | $5.92 \times 10^8$ | 100% |

*0.5 g paste (3.5 g lecithin mixed with 0.7 g *P. acidilactici* NRRL b-5051710 B/g and 4.5 mL olive oil mixture) were transferred into 1 mL liquid juice, heat treated in water bath at 80° C. for designated time. Temperature probe in tube used to determine when internal temperature reaches 80 C. When the temperature of juice reach 80° C., 1) immediately; 2) incubated at 80° C. for 5 minutes, 30 incubated at 80° C. for 10 minutes, then removed the tube from water bath, mixed homogenously by vortex for 30 seconds, and performed series of dilution with saline, and plated 100 ul of desirable dilution onto MRS plates overnight at 37° C. and counted the individual colonies. Temperature was verified with a digital probe.

TABLE 18

Detection of live probiotics after prepared the oat meals with probiotics and lecithin after re-suspended with the hot water.

| Probiotics | Incubation time at 80° C. water bath | # of live *P. acidilactici* (cfu/g)* | % of survival |
|---|---|---|---|
| *P. acidilactici* NRRL B-50517 + lecithin | 82° C. | $2.78 \times 10^8$ | 34.69% |
| | 88° C. | $1.88 \times 10^7$ | 2.35% |
| | 93° C. | $5.88 \times 10^7$ | 7.35% |
| *P. acidilactici* NRRL B-50517 | 88° C. | $1.39 \times 10^6$ | 0.14% |

*28 g oats weighed into autoclaved glass bowl. 1.4 g 10 B/g 5051 mixed with 7 g NOW sunflower lecithin and 9 mL olive oil. 1.1 g 10 B/g 5051 mixed with 10 g Skippy peanut butter. Either 1 g lecithin (0.8 B cfu), PB (1B cfu), or plain 1 B/g 5051 added to each oatmeal bowl (3 each). 118 mL water boiled in microwave, added to each bowl at 82° C., 88 C. and 93 C. Temperature was verified with a digital probe. 1 g oatmeal mixture diluted in 5 mL saline, diluted and plated onto MRS.

Example 9—Effect of Different Amphipathic Products as the Carriers of Probiotics for Heat Treatment In this example, the effect of different amphipathic products were tested for their ability to enhance heat resistance of *Pediococcus acidilactici*.

TABLE 19

Effects of peanut butters as the amphipathic products on the probiotics survival after dry heat treatment.

| Heat treatment temperature | Time of heat treatment | % survival of *P. acidilactici** |
|---|---|---|
| 85° C. | 1 minutes | 96.30% |
| | 2.5 minutes | 98.10% |
| | 5 minutes | 24.10% |
| | 10 minutes | 19.30% |
| | 20 minutes | 2.30% |
| 95° C. | 1 minutes | 26.90% |
| | 2.5 minutes | 29.20% |
| | 5 minutes | 0.52% |
| | 10 minutes | 0.11% |

0.5 g (1 billion cfu/g) mixtures of peanut butter and *P. acidilactici* NRRL B-50517 was place in an Eppendorf tube, and were places at 95° C. and timed for 1 min, 2.5 mins, 5 min, and 10 min. or placed at 85° C. and timed for 1 min, 2.5 mins, 5 min, 10 min and 20 min. Temperature was verified with a digital probe. Added 500 ul of saline, vortex, dilute and plate 100 ul desirable dilution onto MRS plate overnight at 37° C. for viability count. The survival rate was obtained by dividing the numbers of viable cells at the heat treatment by the numbers of viable cells at room temperature (without heat treatment).

TABLE 20

Effects of peanut butters as the amphipathic products on the probiotics survival after wet heat treatment.

| Time of 80° C. hot water treatment | % of survival of P. acidilactici |
|---|---|
| Immediately | 69.00% |
| 1 minutes | 54.70% |
| 2.5 minutes | 20.80% |
| 5 minutes | 20.71% |

0.5 g (1 billion cfu/g) mixtures of P. acidilactici NRRL B-50517 fermentative cultures with peanut butter was place in a 1.5 ml tube that contains 1 ml of distilled water. Place 1.5 ml tubes on heat plate. Time for 5 mins or until temperature reaches 80° C., then time for 1 min, 2.5 mins, and 5 mins. Temperature was verified with a digital probe. After the heat treatment, vortex the samples, dilute and plate 100 ul desirable dilution onto MRS plate overnight at 37° C. for viability count. The survival rate was obtained by dividing the numbers of viable cells at the heat treatment by the numbers of viable cells at room temperature (without heat treatment).

TABLE 21

Effects of different amphipathic products on the probiotics survival after dry heat treatment.

| Amphipathic products | % survival of P. acidilactici* |
|---|---|
| Peanut butters with large chucks | 9.7% |
| Peanut butters | 14.5% |
| Organic peanut butters | 15.49% |
| Almond butters | 24.05% |
| Hazelnut butters | 3.68% |
| Cookie butters | 17.65% |
| Chocolate spread butters | 2.60% |

*Empty tubes were preheated to 85° C. on a hot plate. Temperature was verified with a digital probe. Once empty tubes were heated 0.5 mL (~0.5 g of peanut butter and P. acidilactici NRRL B-50517 mixture (1 billion cfu/g) was added. The mixture was left on the hot plate 85° C. for the 5 minutes. After heating the tubes were left at room temperature for ~10 minutes to cool. Once cooled the mixture was added to 10 mL of saline. Performed the dilution and plate 100 ul desirable dilution onto MRS plate overnight at 37° C. for viability count. The survival rate was obtained by dividing the numbers of viable cells at the heat treatment by the numbers of viable cells at room temperature (without heat treatment).

TABLE 22

Effects of Peanut Butter on improvement of Pediococcus acidilactici NRRL B-50517 survival in different juice after 80° C. heat treatment

| | % survival of acidilactici* | | |
|---|---|---|---|
| Liquids | Immediately | 5 mins at 80° C. | 10 mins at 80° C. |
| Pear | 3.46% | 0.14% | 0.13% |
| Soy Sauce | 40.71% | 14.18% | 0.31% |
| V8 Juice | 4.06% | 0.22% | 0.03% |
| Balsamic Vinaigrette | 25.96% | 0.41% | 0.15% |
| Lemonade | 12.24% | 5.80% | 0.64% |
| Crane Cherry | 7.36% | 7.16% | 1.00% |

*0.5 g mixture of P. acidilactici NRRL B-50517 fermentative cultures and lecithin [prepared by mixing 3.5 g lecithin with 0.7 g P. acidilactici NRRL B-50517 (10 billion cfu/g) and 4.5 mL olive oil]. 0.5 g mixture weighed into 1 mL liquid, heat treated in water bath at 80° C. for designated time. Temperature probe in tube used to determine when internal temperature reaches 80° C. Immediately: immediately after temperature reached, tube removed from water bath. After heating the tubes were left at room temperature for ~10 minutes to cool. Once cooled the mixture was added to 10 mL of saline. Performed the dilution and plate 100 ul desirable dilution onto MRS plate overnight at 37° C. for viability count. The survival rate was obtained by dividing the numbers of viable cells at the heat treatment by the numbers of viable cells at room temperature (without heat treatment).

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A composition comprising a probiotic in admixture with an effective amount of an amphipathic substance, wherein the composition is made by a process comprising:

i) adding an effective amount of the amphipathic substance to a composition comprising the probiotic; and ii) subjecting the composition to heat at a temperature of between 50° C. and 100° C., wherein the amphipathic substance enhances viability of the probiotic in the composition when the composition is subjected to a temperature of at least between 50° C. and 100° C., wherein the ratio (w/w) of the amphipathic substance to the probiotic ranges from about 1:1 to about 25:1, wherein the probiotic is *Pediococcus acidilactici*, and wherein the amphipathic substance comprises lecithin, peanut butter, almond butter, soy butter or cookie butter.

2. The composition of claim 1, further comprising an oil that is mixed with the amphipathic substance and probiotic.

3. The composition of claim 1, wherein the composition forms a lipid paste and the amphipathic substance serves as the carrier for the probiotic.

4. The composition of claim 1, wherein the probiotic is *Pediococcus acidilactici* NRRL B-50517.

5. The composition of claim 1, wherein the composition is subjected to a temperature of between 65° C.-100° C.

6. The composition of claim 1, wherein the ratio (w/w) of the amphipathic substance to the probiotic ranges from about 1:1 to about 10:1.

7. The composition of claim 1, wherein the ratio (w/w) of the amphipathic substance to the probiotic ranges from about 10:1 to about 25:1.

* * * * *